US012667440B2

(12) United States Patent
Hassan et al.

(10) Patent No.: US 12,667,440 B2
(45) Date of Patent: Jun. 30, 2026

(54) FOOT PEDAL ASSEMBLIES WITH INDICATORS FOR ROBOTIC MEDICAL SYSTEMS

(71) Applicant: Auris Health, Inc., Redwood City, CA (US)

(72) Inventors: Alexander Tarek Hassan, San Francisco, CA (US); Eloi Le Roux, San Francisco, CA (US)

(73) Assignee: AURIS HEALTH, INC., Redwood City, CA (US)

( * ) Notice: Subject to any disclaimer, the term of this patent is extended or adjusted under 35 U.S.C. 154(b) by 1040 days.

(21) Appl. No.: 17/137,993

(22) Filed: Dec. 30, 2020

(65) Prior Publication Data

US 2021/0205040 A1 Jul. 8, 2021

Related U.S. Application Data

(60) Provisional application No. 62/956,819, filed on Jan. 3, 2020.

(51) Int. Cl.
| | |
|---|---|
| *A61B 34/20* | (2016.01) |
| *A61B 34/00* | (2016.01) |
| *A61B 34/37* | (2016.01) |
| *B25J 9/00* | (2006.01) |
| *B25J 13/04* | (2006.01) |
| *B25J 19/00* | (2006.01) |

(52) U.S. Cl.
CPC .............. *A61B 34/37* (2016.02); *A61B 34/20* (2016.02); *A61B 34/76* (2016.02); *B25J*

*9/0009* (2013.01); *B25J 19/0025* (2013.01); *A61B 2034/2055* (2016.02)

(58) Field of Classification Search
CPC ................. B25J 9/0009; B25J 19/0025; A61B 2034/2055
See application file for complete search history.

(56) References Cited

U.S. PATENT DOCUMENTS

| | | | |
|---|---|---|---|
| 7,781,941 | B2 | 8/2010 | Horvath et al. |
| 8,120,301 | B2 | 2/2012 | Goldberg et al. |
| 8,398,541 | B2 | 3/2013 | DiMaio et al. |
| 8,418,073 | B2 | 4/2013 | Mohr et al. |
| 8,423,182 | B2 | 4/2013 | Robinson et al. |
| 8,600,551 | B2 | 12/2013 | Itkowitz et al. |

(Continued)

FOREIGN PATENT DOCUMENTS

WO WO-2018217522 A1 * 11/2018 ............. A61B 34/30

*Primary Examiner* — Benjamin J Klein
*Assistant Examiner* — Thien Jason Tran
(74) *Attorney, Agent, or Firm* — FBT Gibbons LLP

(57) ABSTRACT

A medical system can include a foot pedal assembly that includes one or more pedals configured to be foot operated for controlling various function of the system. A dynamic indicator can be associated with a first pedal of the one or more pedals. The dynamic indicator can be configured to provide a first indication when the medical system is in a first state, and provide a second indication when the medical system is in a second state. The system can further be configured to determine a state of the medical system, cause the dynamic indicator to provide the first indication in response to the determined state comprising the first state, and cause the dynamic indicator to provide the second indication in response to the determined state comprising the second state.

17 Claims, 30 Drawing Sheets

(56) References Cited

U.S. PATENT DOCUMENTS

| | | | |
|---|---|---|---|
| 9,043,027 | B2 | 5/2015 | Durant et al. |
| 9,888,973 | B2 | 2/2018 | Olson et al. |
| 2010/0228264 | A1* | 9/2010 | Robinson ........... A61B 18/1206 |
| | | | 606/130 |
| 2012/0059390 | A1* | 3/2012 | Mintz ................... A61B 34/25 |
| | | | 606/130 |
| 2013/0103050 | A1* | 4/2013 | Richmond ........... A61B 17/285 |
| | | | 606/130 |
| 2017/0252113 | A1 | 9/2017 | Beelen et al. |
| 2018/0132948 | A1 | 5/2018 | Mercado |
| 2018/0221100 | A1 | 8/2018 | Berry et al. |
| 2018/0280099 | A1 | 10/2018 | Cone et al. |
| 2018/0353247 | A1 | 12/2018 | Ishihara et al. |
| 2019/0110845 | A1* | 4/2019 | Yang ...................... A61B 18/24 |
| 2020/0078111 | A1* | 3/2020 | Oberkircher ........... A61B 34/74 |
| 2020/0289222 | A1* | 9/2020 | Denlinger .............. B25J 9/1664 |

* cited by examiner

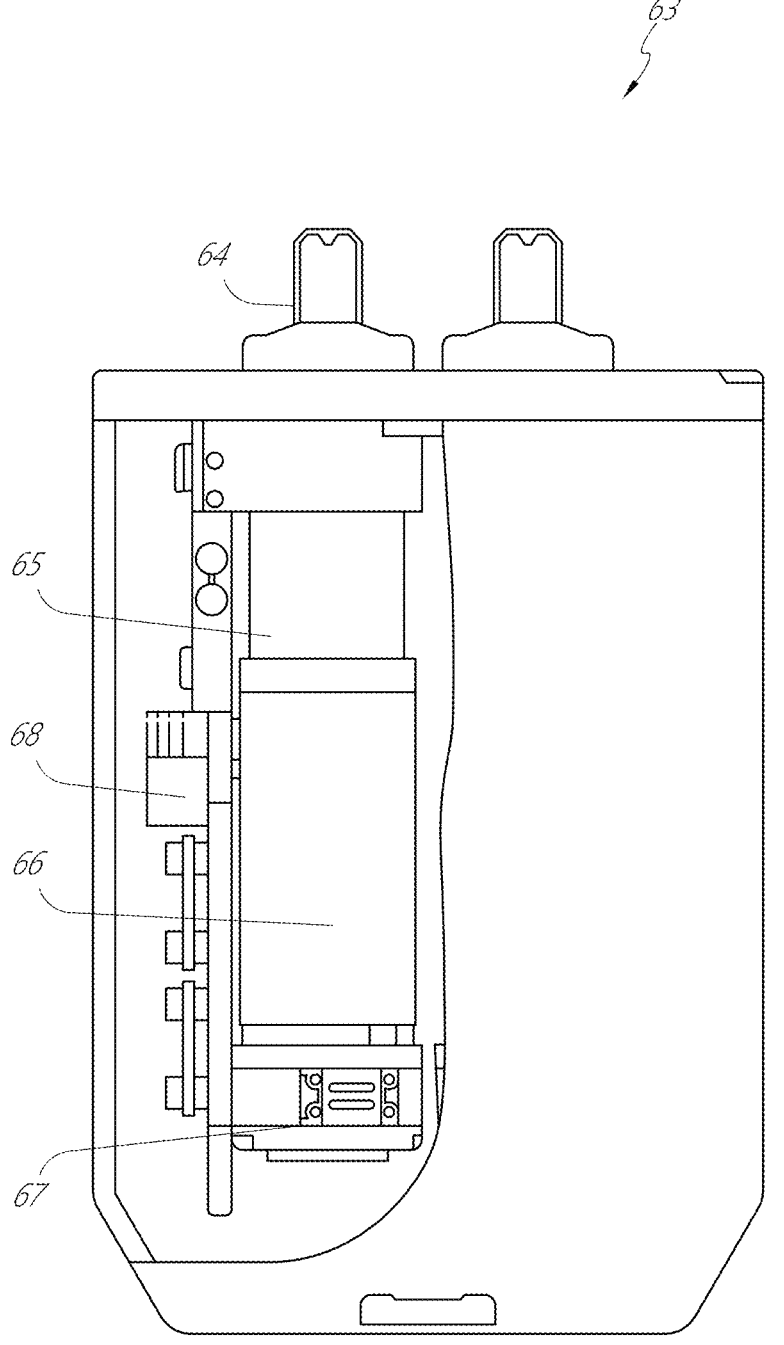
FIG. 15

205

207    209    207    211

207

211

211    207

205

207    209    211

Foot Pedals Inactive

207

207

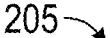
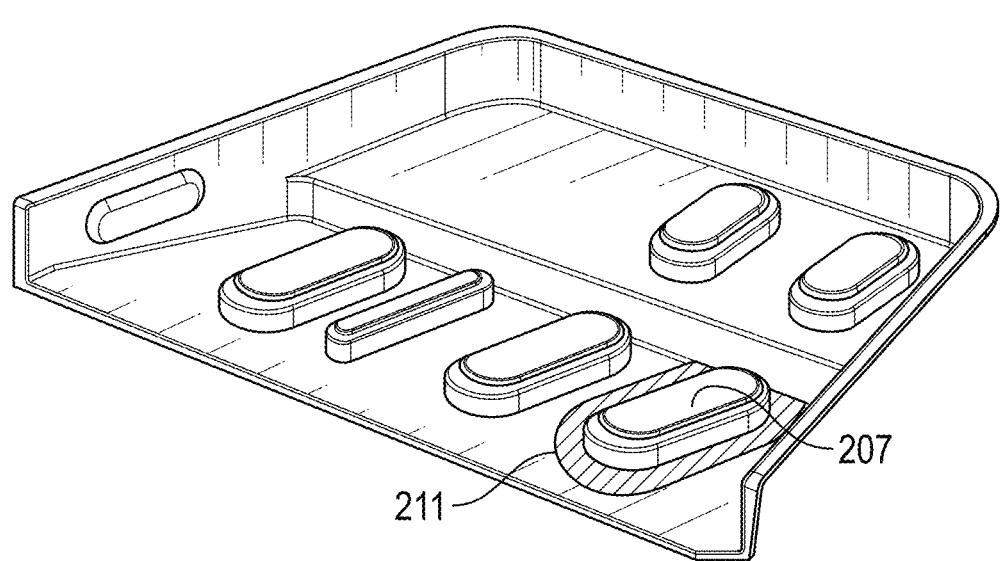
FIG. 24A
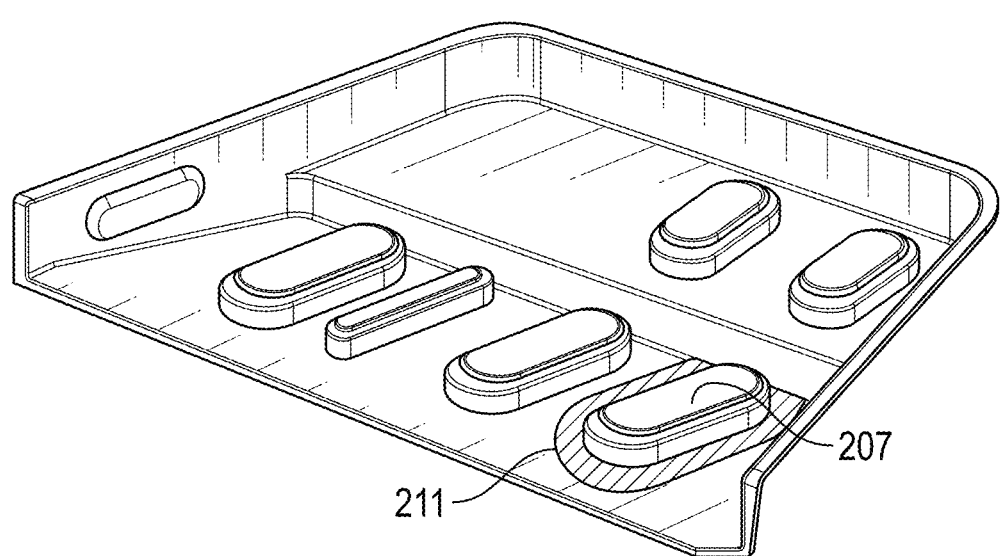
FIG. 24B

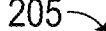
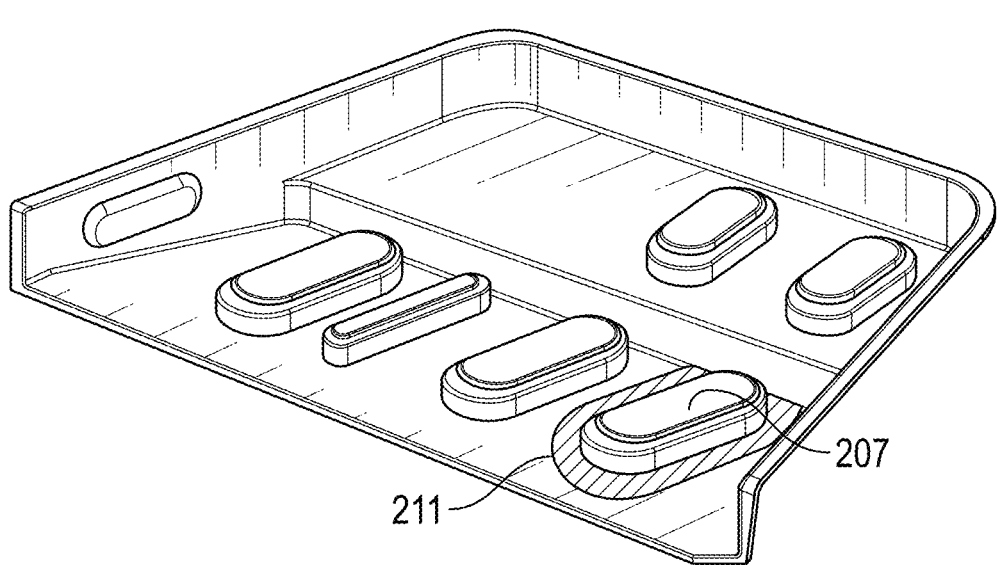
FIG. 24C

205

205

205

215

Stapler Activation Ready

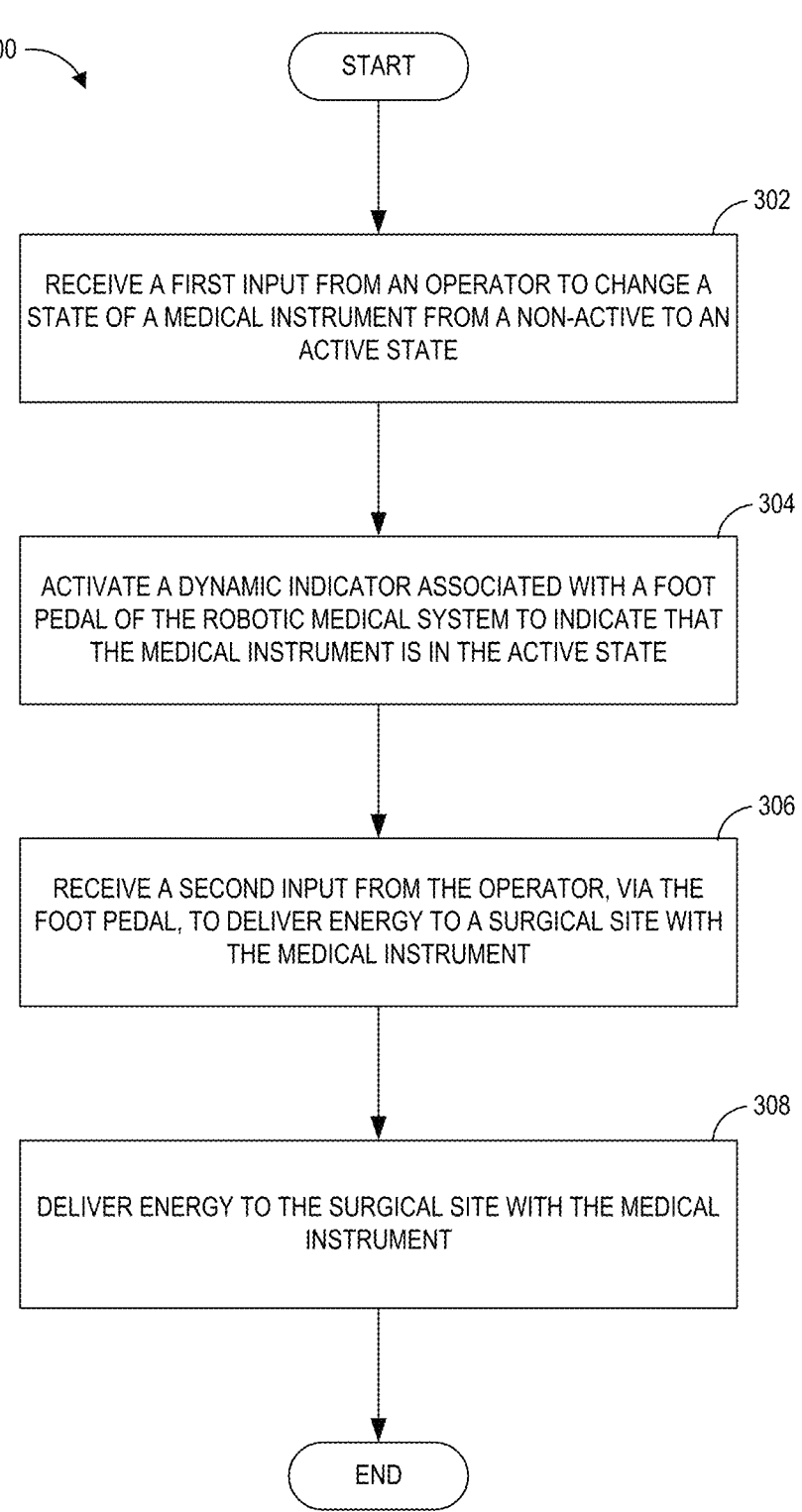

300

START

302

RECEIVE A FIRST INPUT FROM AN OPERATOR TO CHANGE A STATE OF A MEDICAL INSTRUMENT FROM A NON-ACTIVE TO AN ACTIVE STATE

304

ACTIVATE A DYNAMIC INDICATOR ASSOCIATED WITH A FOOT PEDAL OF THE ROBOTIC MEDICAL SYSTEM TO INDICATE THAT THE MEDICAL INSTRUMENT IS IN THE ACTIVE STATE

306

RECEIVE A SECOND INPUT FROM THE OPERATOR, VIA THE FOOT PEDAL, TO DELIVER ENERGY TO A SURGICAL SITE WITH THE MEDICAL INSTRUMENT

308

DELIVER ENERGY TO THE SURGICAL SITE WITH THE MEDICAL INSTRUMENT

END

FIG. 29

FOOT PEDAL ASSEMBLIES WITH INDICATORS FOR ROBOTIC MEDICAL SYSTEMS

PRIORITY APPLICATION

This application claims priority to U.S. Provisional Patent Application No. 62/956,819, filed Jan. 3, 2020, which is incorporated herein by reference. Any and all applications for which a foreign or domestic priority claim is identified in the Application Data Sheet as filed with the present application are hereby incorporated by reference under 37 CFR 1.57.

NAMES OF PARTIES TO A JOINT RESEARCH AGREEMENT

The subject matter described herein was developed under a joint research agreement, to which the following are relevant parties:
Auris Health, Inc.
Ethicon LLC

TECHNICAL FIELD

This application is directed to robotic medical systems, and more particularly, to foot pedal assemblies with dynamic visual indicators configured for use with robotic medical systems.

BACKGROUND

Medical procedures, such as laparoscopy or endoscopy, may involve accessing and visualizing an internal region of a patient. In a laparoscopic procedure, for example, a medical instrument can be inserted into an internal region through a laparoscopic access port. Robotically-enabled medical system can be used to perform such medical procedures. The robotically-enabled medical systems may include several robotic components, including, for example, robotic arms, robotic instrument manipulators, and robotic medical instruments, such as robotically controllable laparoscopes or endoscopes. The robotically-enabled medical systems can be controlled using a user console that may include one or more hand operated inputs as well as one or more foot operated inputs.

SUMMARY

In a first aspect, a medical system can include a foot pedal assembly comprising one or more pedals configured to be foot operated, and a dynamic indicator associated with a first pedal of the one or more pedals. The dynamic indicator can be configured to provide a first indication when the medical system is in a first state, and provide a second indication when the medical system is in a second state. The system can also include a processor in communication with memory stored instructions that, when executed, cause the processor to determine a state of the medical system, cause the dynamic indicator to provide the first indication in response to the determined state comprising the first state, and cause the dynamic indicator to provide the second indication in response to the determined state comprising the second state.

The medical system can include one or more of the following features in any combination: (a) wherein the medical system comprises a robotic medical system; (b) at least one robotic arm configured to perform a surgical procedure, and a robotic medical instrument coupled to the at least one robotic arm; (c) wherein the robotic medical instrument comprises an energy-delivery instrument, and the processor is further configured to determine an instrument status indicative of the energy-delivery instrument being in a ready state for energy delivery, and provide the first indication that the medical system is in the first state based on the determined instrument status being in the ready state for energy deliver; (d) wherein the instructions, when executed, further cause the processor to determine the state of the medical system based on one or more of the following a user input, a state of the at least one robotic arm, a state of the robotic medical instrument, and a state of the first pedal; (e) wherein the dynamic indicator comprises a dynamic visual indicator and the first indication comprises a lit state of the dynamic visual indicator; (f) wherein the dynamic visual indicator comprises a light; (g) wherein the light is configured such that the first indication comprises a first color and the second indication comprises a second color; (h) wherein the first indication is indicative that the energy-delivery instrument is in the ready state for energy delivery, and the second indication is indicative that the energy-delivery instrument has been unloaded; (i) wherein the dynamic indicator is a haptic indicator, or the dynamic indicator is a sound-based indicator; (j) wherein at least one of the first indication and the second indication are associated with an instrument function activation; and/or (k) wherein the instrument function activation comprises activation of at least one of: stapling, suction, irrigation, a suture cutting mode, and a variable grip force move or a robotic medical instrument.

In another aspect, a foot-operated pedal assembly for a medical system can include a housing, a plurality of pedals on the housing, the plurality of pedals configured to be foot operated, and a plurality of dynamic indicators, each dynamic indicator of the plurality of dynamic indicators associated with one pedal of the plurality of pedals. Each dynamic indicator can be configured to provide a first indication when the medical system is in a first state, and provide a second indication when the medical system is in a second state.

The pedal assembly can include one or more of the following features in any combination: (a) wherein the dynamic indicator comprises a light, the first indication comprises an unlit state of the light, and the second indication comprises a lit state of the light; (b) wherein the dynamic indicator comprises a light, the first indication comprises a first lit state of the light, wherein the first lit state comprises a first color, and the second indication comprises a second lit state of the light, wherein the second lit state comprises a second color; (c) wherein the dynamic indicator comprises a light and at least one of the first indication and the second indication comprises a first pattern of activating and deactivating the light, a first brightness of the light, or a first color of the light; (d) wherein the other of the first indication and the second indication comprises a second pattern of activating and deactivating the light, a second brightness of the light, or a second color of the light; (e) wherein a first pedal of the plurality of pedals is selectively actuable between a deactivated state and an activated state, and the assembly indicator is configured to provide the first indication, the second indication, and a third indication; and/or (f) wherein the deactivated state comprises an unpressed state of the first pedal, and the activated state comprises a pressed state of the first pedal.

In another aspect, a method operable by a robotic medical system is disclosed. The method can include receiving a first input from an operator to change a state of a medical instrument from a non-active to an active state; activating a dynamic indicator associated with a foot pedal of the robotic medical system to indicate that the medical instrument is in the active state; receiving a second input from the operator, via the foot pedal, to deliver energy to a surgical site with the medical instrument; and delivering energy to the surgical site with the medical instrument.

The method can include one or more of the following features in any combination: (a) wherein the dynamic indicator continues to be active while delivering energy from the instrument to the surgical site; (b) wherein the dynamic indicator comprises a light, and activating the dynamic indicator comprises illuminating the food pedal with the light; (c) wherein the first input is associated with the operator stepping on the foot pedal; (d) wherein the second input is associated with the operator stepping on the foot pedal; (e) wherein at least one dynamic indicator comprises a visual indicator; and/or (f) wherein at least one dynamic indicator comprises a haptic indicator.

In another aspect, a method includes determining a first state of a robotic medical system; providing, with an indicator associated with a foot-operated pedal of the robotic medical system, a first indication based on the first state of the robotic medical system; determining a state change for the robotic medical system from the first state to a second state based on an input; and providing, with the indicator, a second indication based on the second state of the robotic medical system.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

FIG. 15 illustrates an exemplary instrument driver.

FIGS. 24A, 24B, and 24C illustrate examples of an embodiment of a pedal assembly including dynamic visual indicators configured to provide a constant indication.

FIG. 29 is a flow chart depicting a first example method for implementing dynamic indicators for a robotic medical system.

DETAILED DESCRIPTION

1. Overview.

Aspects of the present disclosure may be integrated into a robotically-enabled medical system capable of performing a variety of medical procedures, including both minimally invasive, such as laparoscopy, and non-invasive, such as endoscopy, procedures. Among endoscopic procedures, the system may be capable of performing bronchoscopy, ureteroscopy, gastroscopy, etc.

In addition to performing the breadth of procedures, the system may provide additional benefits, such as enhanced imaging and guidance to assist the physician. Additionally, the system may provide the physician with the ability to perform the procedure from an ergonomic position without the need for awkward arm motions and positions. Still further, the system may provide the physician with the ability to perform the procedure with improved ease of use such that one or more of the instruments of the system can be controlled by a single user.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto. Such concepts may have applicability throughout the entire specification.

A. Robotic System—Cart.

Figure 1:
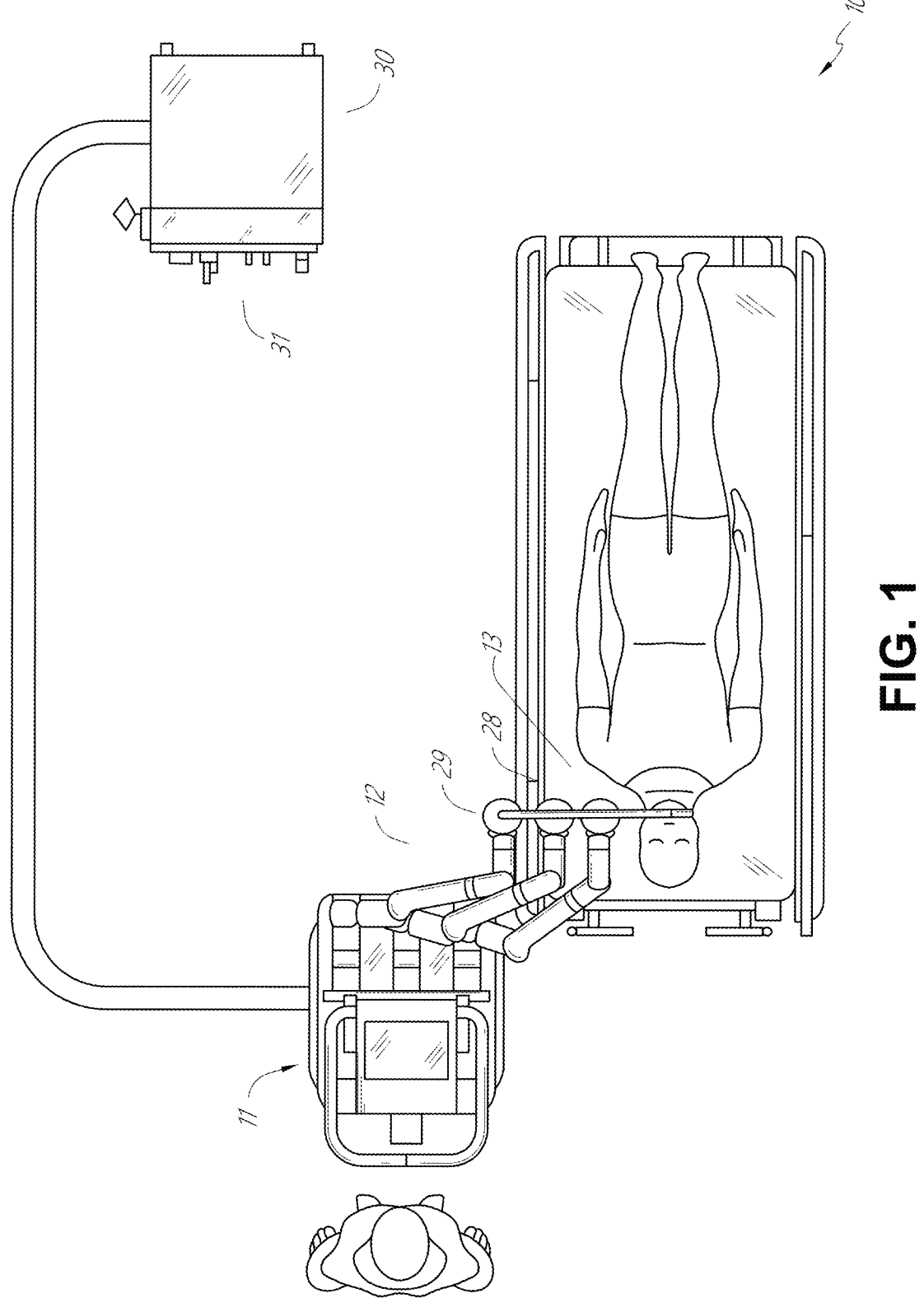
FIG. 1 illustrates an embodiment of a cart-based robotic system arranged for diagnostic and/or therapeutic bronchoscopy.
Figure 2:
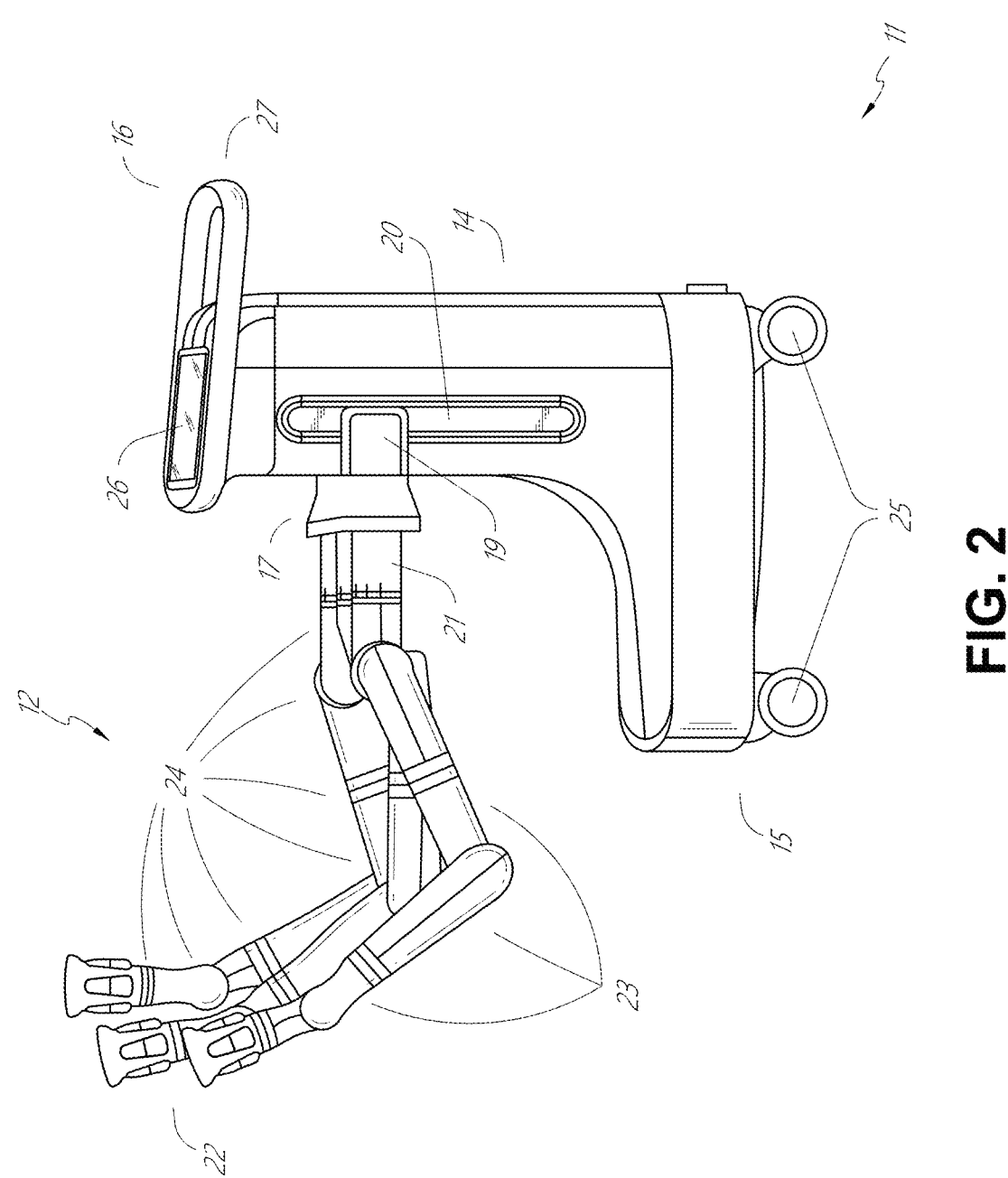
FIG. 2 depicts further aspects of the robotic system of FIG. 1.

The robotically-enabled medical system may be configured in a variety of ways depending on the particular procedure. FIG. 1 illustrates an embodiment of a cart-based robotically-enabled system 10 arranged for a diagnostic and/or therapeutic bronchoscopy. During a bronchoscopy, the system 10 may comprise a cart 11 having one or more robotic arms 12 to deliver a medical instrument, such as a steerable endoscope 13, which may be a procedure-specific bronchoscope for bronchoscopy, to a natural orifice access point (i.e., the mouth of the patient positioned on a table in the present example) to deliver diagnostic and/or therapeutic tools. As shown, the cart 11 may be positioned proximate to the patient's upper torso in order to provide access to the access point. Similarly, the robotic arms 12 may be actuated to position the bronchoscope relative to the access point. The arrangement in FIG. 1 may also be utilized when performing a gastro-intestinal (GI) procedure with a gastroscope, a specialized endoscope for GI procedures. FIG. 2 depicts an example embodiment of the cart in greater detail.

With continued reference to FIG. 1, once the cart 11 is properly positioned, the robotic arms 12 may insert the steerable endoscope 13 into the patient robotically, manually, or a combination thereof. As shown, the steerable endoscope 13 may comprise at least two telescoping parts, such as an inner leader portion and an outer sheath portion, each portion coupled to a separate instrument driver from the set of instrument drivers 28, each instrument driver coupled to the distal end of an individual robotic arm. This linear arrangement of the instrument drivers 28, which facilitates coaxially aligning the leader portion with the sheath portion, creates a "virtual rail" 29 that may be repositioned in space by manipulating the one or more robotic arms 12 into different angles and/or positions. The virtual rails described herein are depicted in the Figures using dashed lines, and accordingly the dashed lines do not depict any physical structure of the system. Translation of the instrument drivers 28 along the virtual rail 29 telescopes the inner leader portion relative to the outer sheath portion or advances or retracts the endoscope 13 from the patient. The angle of the virtual rail 29 may be adjusted, translated, and pivoted based on clinical application or physician preference. For example, in bronchoscopy, the angle and position of the virtual rail 29 as shown represents a compromise between providing physician access to the endoscope 13 while minimizing friction that results from bending the endoscope 13 into the patient's mouth.

The endoscope 13 may be directed down the patient's trachea and lungs after insertion using precise commands from the robotic system until reaching the target destination or operative site. In order to enhance navigation through the patient's lung network and/or reach the desired target, the endoscope 13 may be manipulated to telescopically extend the inner leader portion from the outer sheath portion to obtain enhanced articulation and greater bend radius. The use of separate instrument drivers 28 also allows the leader portion and sheath portion to be driven independently of each other.

For example, the endoscope 13 may be directed to deliver a biopsy needle to a target, such as, for example, a lesion or nodule within the lungs of a patient. The needle may be deployed down a working channel that runs the length of the endoscope to obtain a tissue sample to be analyzed by a pathologist. Depending on the pathology results, additional tools may be deployed down the working channel of the endoscope for additional biopsies. After identifying a nodule to be malignant, the endoscope 13 may endoscopically deliver tools to resect the potentially cancerous tissue. In some instances, diagnostic and therapeutic treatments can be delivered in separate procedures. In those circumstances, the endoscope 13 may also be used to deliver a fiducial to "mark" the location of the target nodule as well. In other instances, diagnostic and therapeutic treatments may be delivered during the same procedure.

The system 10 may also include a movable tower 30, which may be connected via support cables to the cart 11 to provide support for controls, electronics, fluidics, optics, sensors, and/or power to the cart 11. Placing such functionality in the tower 30 allows for a smaller form factor cart 11 that may be more easily adjusted and/or re-positioned by an operating physician and his/her staff. Additionally, the division of functionality between the cart/table and the support tower 30 reduces operating room clutter and facilitates improving clinical workflow. While the cart 11 may be positioned close to the patient, the tower 30 may be stowed in a remote location to stay out of the way during a procedure.

In support of the robotic systems described above, the tower 30 may include component(s) of a computer-based control system that stores computer program instructions, for example, within a non-transitory computer-readable storage medium such as a persistent magnetic storage drive, solid state drive, etc. The execution of those instructions, whether the execution occurs in the tower 30 or the cart 11, may control the entire system or sub-system(s) thereof. For example, when executed by a processor of the computer system, the instructions may cause the components of the robotics system to actuate the relevant carriages and arm mounts, actuate the robotics arms, and control the medical instruments. For example, in response to receiving the control signal, the motors in the joints of the robotics arms may position the arms into a certain posture.

The tower 30 may also include a pump, flow meter, valve control, and/or fluid access in order to provide controlled irrigation and aspiration capabilities to the system that may be deployed through the endoscope 13. These components may also be controlled using the computer system of the tower 30. In some embodiments, irrigation and aspiration capabilities may be delivered directly to the endoscope 13 through separate cable(s).

The tower 30 may include a voltage and surge protector designed to provide filtered and protected electrical power to the cart 11, thereby avoiding placement of a power transformer and other auxiliary power components in the cart 11, resulting in a smaller, more moveable cart 11.

The tower 30 may also include support equipment for the sensors deployed throughout the robotic system 10. For example, the tower 30 may include optoelectronics equipment for detecting, receiving, and processing data received from the optical sensors or cameras throughout the robotic system 10. In combination with the control system, such optoelectronics equipment may be used to generate real-time images for display in any number of consoles deployed throughout the system, including in the tower 30. Similarly, the tower 30 may also include an electronic subsystem for receiving and processing signals received from deployed electromagnetic (EM) sensors. The tower 30 may also be used to house and position an EM field generator for detection by EM sensors in or on the medical instrument.

The tower 30 may also include a console 31 in addition to other consoles available in the rest of the system, e.g., console mounted on top of the cart. The console 31 may include a user interface and a display screen, such as a touchscreen, for the physician operator. Consoles in the system 10 are generally designed to provide both robotic controls as well as preoperative and real-time information of the procedure, such as navigational and localization information of the endoscope 13. When the console 31 is not the only console available to the physician, it may be used by a second operator, such as a nurse, to monitor the health or vitals of the patient and the operation of the system 10, as well as to provide procedure-specific data, such as navigational and localization information. In other embodiments, the console 30 is housed in a body that is separate from the tower 30.

The tower 30 may be coupled to the cart 11 and endoscope 13 through one or more cables or connections (not shown). In some embodiments, the support functionality from the tower 30 may be provided through a single cable to the cart 11, simplifying and de-cluttering the operating room. In other embodiments, specific functionality may be coupled in separate cabling and connections. For example, while power may be provided through a single power cable to the cart 11, the support for controls, optics, fluidics, and/or navigation may be provided through a separate cable.

FIG. 2 provides a detailed illustration of an embodiment of the cart 11 from the cart-based robotically-enabled system shown in FIG. 1. The cart 11 generally includes an elongated support structure 14 (often referred to as a "column"), a cart base 15, and a console 16 at the top of the column 14. The column 14 may include one or more carriages, such as a carriage 17 (alternatively "arm support") for supporting the deployment of one or more robotic arms 12 (three shown in FIG. 2). The carriage 17 may include individually configurable arm mounts that rotate along a perpendicular axis to adjust the base of the robotic arms 12 for better positioning relative to the patient. The carriage 17 also includes a carriage interface 19 that allows the carriage 17 to vertically translate along the column 14.

The carriage interface 19 is connected to the column 14 through slots, such as slot 20, that are positioned on opposite sides of the column 14 to guide the vertical translation of the carriage 17. The slot 20 contains a vertical translation interface to position and hold the carriage 17 at various vertical heights relative to the cart base 15. Vertical translation of the carriage 17 allows the cart 11 to adjust the reach of the robotic arms 12 to meet a variety of table heights, patient sizes, and physician preferences. Similarly, the individually configurable arm mounts on the carriage 17 allow the robotic arm base 21 of the robotic arms 12 to be angled in a variety of configurations.

In some embodiments, the slot 20 may be supplemented with slot covers that are flush and parallel to the slot surface to prevent dirt and fluid ingress into the internal chambers of the column 14 and the vertical translation interface as the carriage 17 vertically translates. The slot covers may be deployed through pairs of spring spools positioned near the vertical top and bottom of the slot 20. The covers are coiled within the spools until deployed to extend and retract from their coiled state as the carriage 17 vertically translates up and down. The spring-loading of the spools provides force to retract the cover into a spool when the carriage 17 translates towards the spool, while also maintaining a tight seal when the carriage 17 translates away from the spool. The covers may be connected to the carriage 17 using, for example, brackets in the carriage interface 19 to ensure proper extension and retraction of the cover as the carriage 17 translates.

The column 14 may internally comprise mechanisms, such as gears and motors, that are designed to use a vertically aligned lead screw to translate the carriage 17 in a mechanized fashion in response to control signals generated in response to user inputs, e.g., inputs from the console 16.

The robotic arms 12 may generally comprise robotic arm bases 21 and end effectors 22, separated by a series of linkages 23 that are connected by a series of joints 24, each joint comprising an independent actuator, each actuator comprising an independently controllable motor. Each independently controllable joint represents an independent degree of freedom available to the robotic arm 12. Each of the robotic arms 12 may have seven joints, and thus provide seven degrees of freedom. A multitude of joints result in a multitude of degrees of freedom, allowing for "redundant" degrees of freedom. Having redundant degrees of freedom allows the robotic arms 12 to position their respective end effectors 22 at a specific position, orientation, and trajectory in space using different linkage positions and joint angles. This allows for the system to position and direct a medical instrument from a desired point in space while allowing the physician to move the arm joints into a clinically advantageous position away from the patient to create greater access, while avoiding arm collisions.

The cart base 15 balances the weight of the column 14, carriage 17, and robotic arms 12 over the floor. Accordingly, the cart base 15 houses heavier components, such as electronics, motors, power supply, as well as components that either enable movement and/or immobilize the cart 11. For example, the cart base 15 includes rollable wheel-shaped casters 25 that allow for the cart 11 to easily move around the room prior to a procedure. After reaching the appropriate position, the casters 25 may be immobilized using wheel locks to hold the cart 11 in place during the procedure.

Positioned at the vertical end of the column 14, the console 16 allows for both a user interface for receiving user input and a display screen (or a dual-purpose device such as, for example, a touchscreen 26) to provide the physician user with both preoperative and intraoperative data. Potential preoperative data on the touchscreen 26 may include preoperative plans, navigation and mapping data derived from preoperative computerized tomography (CT) scans, and/or notes from preoperative patient interviews. Intraoperative data on display may include optical information provided from the tool, sensor and coordinate information from sensors, as well as vital patient statistics, such as respiration, heart rate, and/or pulse. The console 16 may be positioned and tilted to allow a physician to access the console 16 from the side of the column 14 opposite the carriage 17. From this position, the physician may view the console 16, robotic arms 12, and patient while operating the console 16 from behind the cart 11. As shown, the console 16 also includes a handle 27 to assist with maneuvering and stabilizing the cart 11.

Figure 3:
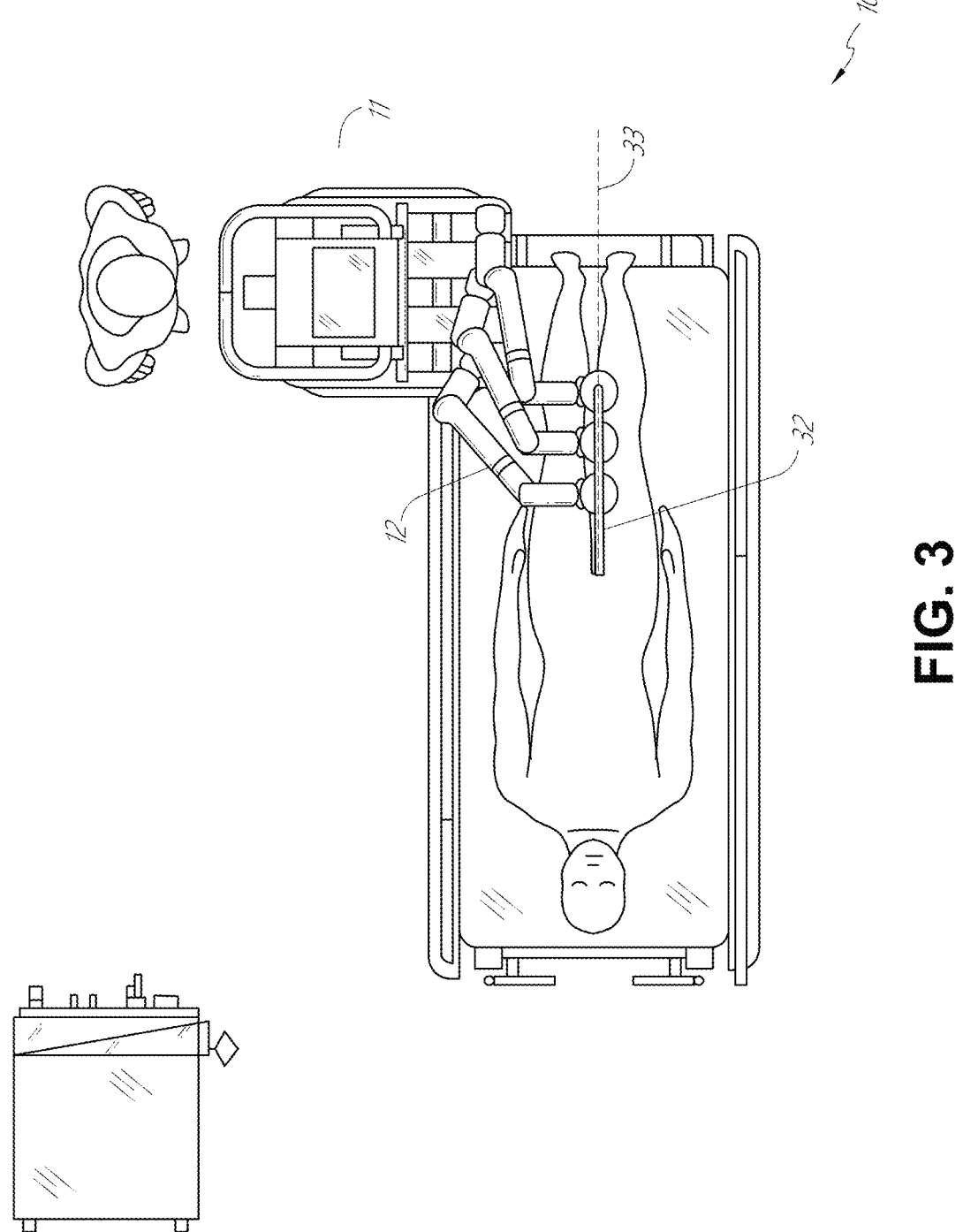
FIG. 3 illustrates an embodiment of the robotic system of FIG. 1 arranged for ureteroscopy.

FIG. 3 illustrates an embodiment of a robotically-enabled system 10 arranged for ureteroscopy. In a ureteroscopic procedure, the cart 11 may be positioned to deliver a ureteroscope 32, a procedure-specific endoscope designed to traverse a patient's urethra and ureter, to the lower abdominal area of the patient. In a ureteroscopy, it may be desirable for the ureteroscope 32 to be directly aligned with the patient's urethra to reduce friction and forces on the sensitive anatomy in the area. As shown, the cart 11 may be aligned at the foot of the table to allow the robotic arms 12 to position the ureteroscope 32 for direct linear access to the patient's urethra. From the foot of the table, the robotic arms 12 may insert the ureteroscope 32 along the virtual rail 33 directly into the patient's lower abdomen through the urethra.

After insertion into the urethra, using similar control techniques as in bronchoscopy, the ureteroscope 32 may be navigated into the bladder, ureters, and/or kidneys for diagnostic and/or therapeutic applications. For example, the ureteroscope 32 may be directed into the ureter and kidneys to break up kidney stone build up using a laser or ultrasonic lithotripsy device deployed down the working channel of the ureteroscope 32. After lithotripsy is complete, the resulting stone fragments may be removed using baskets deployed down the ureteroscope 32.

Figure 4:
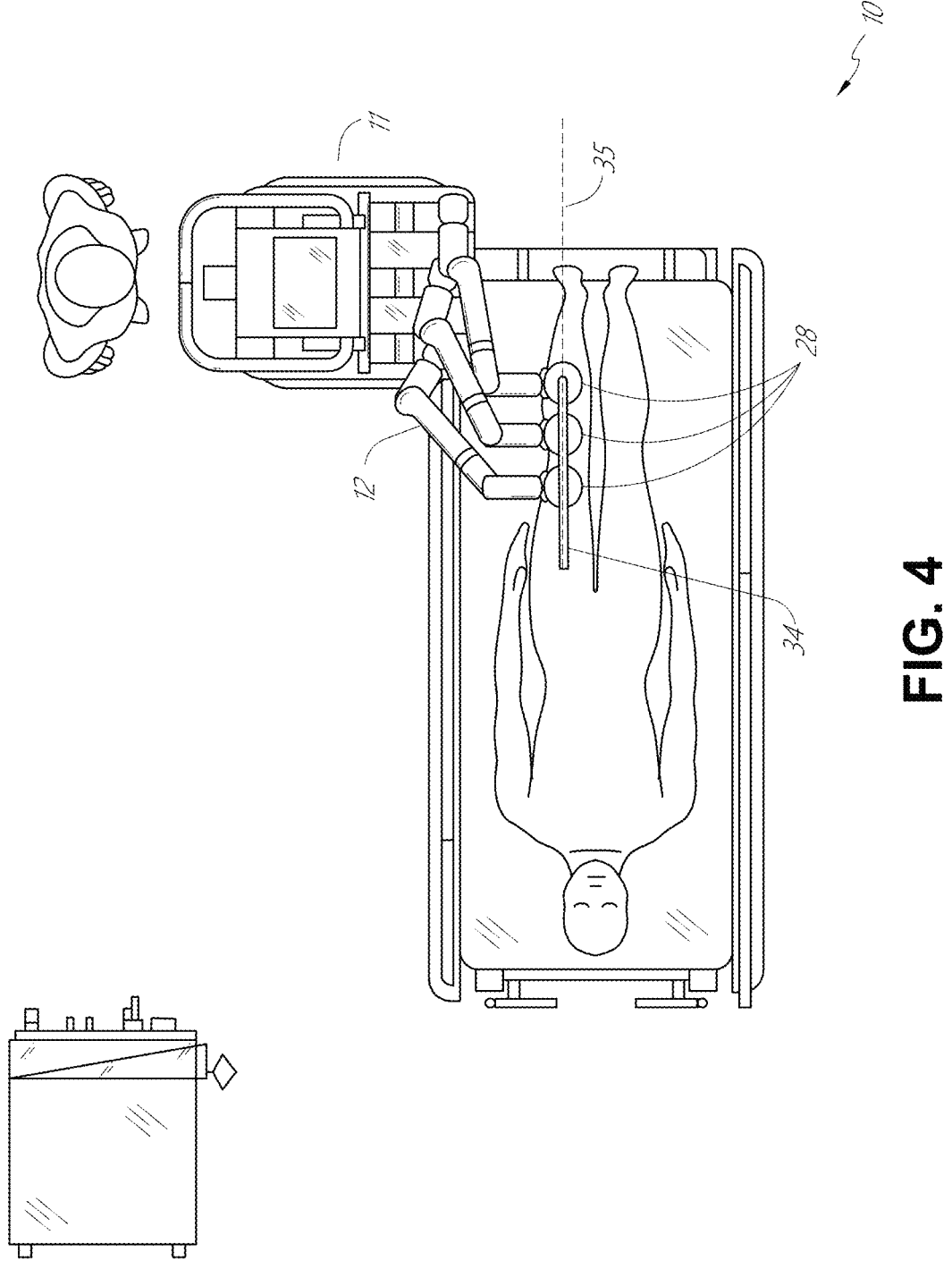
FIG. 4 illustrates an embodiment of the robotic system of FIG. 1 arranged for a vascular procedure.

FIG. 4 illustrates an embodiment of a robotically-enabled system 10 similarly arranged for a vascular procedure. In a vascular procedure, the system 10 may be configured such that the cart 11 may deliver a medical instrument 34, such as a steerable catheter, to an access point in the femoral artery in the patient's leg. The femoral artery presents both a larger diameter for navigation as well as a relatively less circuitous and tortuous path to the patient's heart, which simplifies navigation. As in a ureteroscopic procedure, the cart 11 may be positioned towards the patient's legs and lower abdomen to allow the robotic arms 12 to provide a virtual rail 35 with direct linear access to the femoral artery access point in the patient's thigh/hip region. After insertion into the artery, the medical instrument 34 may be directed and inserted by translating the instrument drivers 28. Alternatively, the cart may be positioned around the patient's upper abdomen in order to reach alternative vascular access points, such as, for example, the carotid and brachial arteries near the shoulder and wrist.

B. Robotic System—Table.

Figure 5:
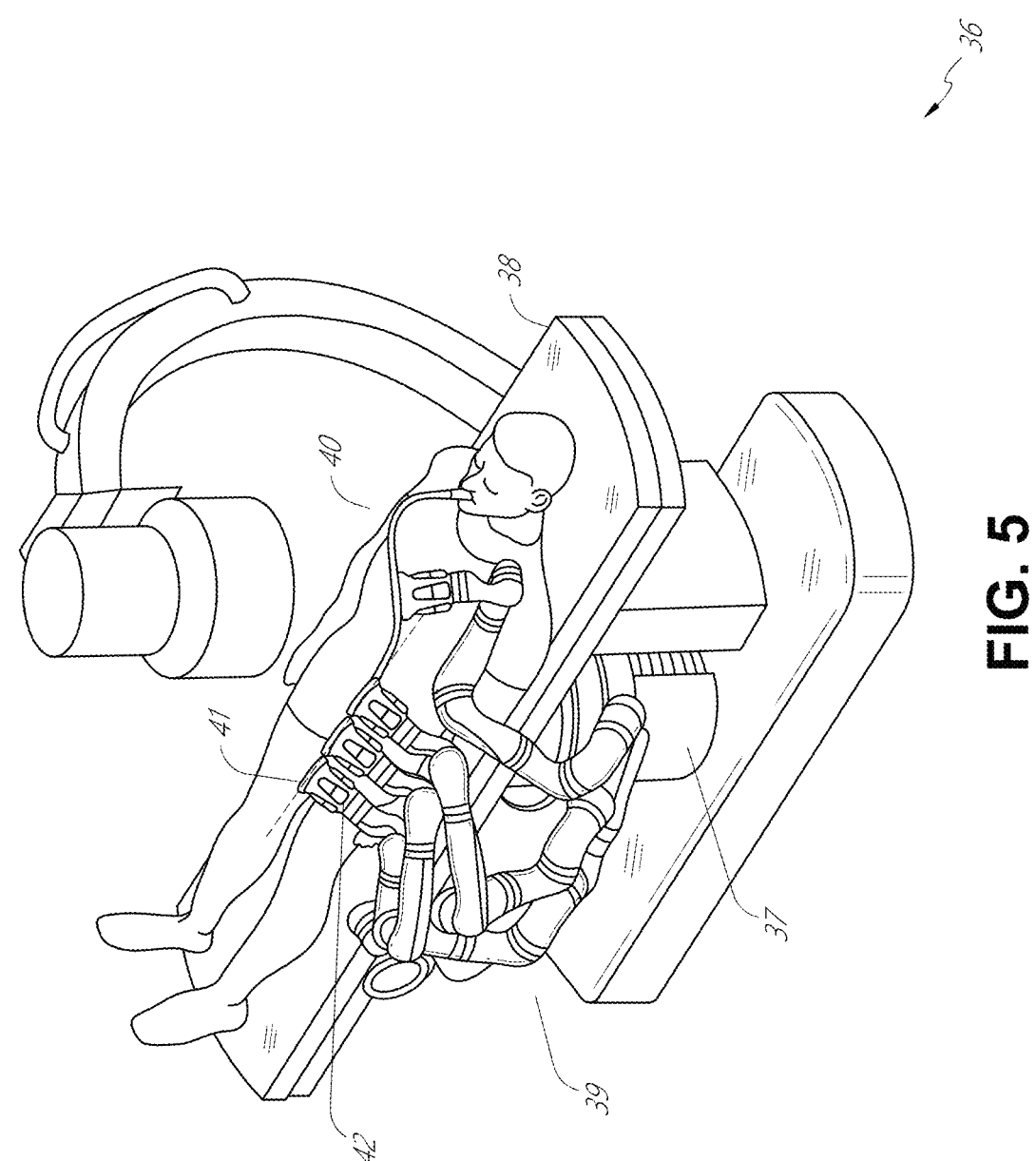
FIG. 5 illustrates an embodiment of a table-based robotic system arranged for a bronchoscopic procedure.

Embodiments of the robotically-enabled medical system may also incorporate the patient's table. Incorporation of the table reduces the amount of capital equipment within the operating room by removing the cart, which allows greater access to the patient. FIG. 5 illustrates an embodiment of such a robotically-enabled system arranged for a bronchoscopic procedure. System 36 includes a support structure or column 37 for supporting platform 38 (shown as a "table" or "bed") over the floor. Much like in the cart-based systems, the end effectors of the robotic arms 39 of the system 36 comprise instrument drivers 42 that are designed to manipulate an elongated medical instrument, such as a bronchoscope 40 in FIG. 5, through or along a virtual rail 41 formed from the linear alignment of the instrument drivers 42. In practice, a C-arm for providing fluoroscopic imaging may be positioned over the patient's upper abdominal area by placing the emitter and detector around the table 38.

Figure 6:
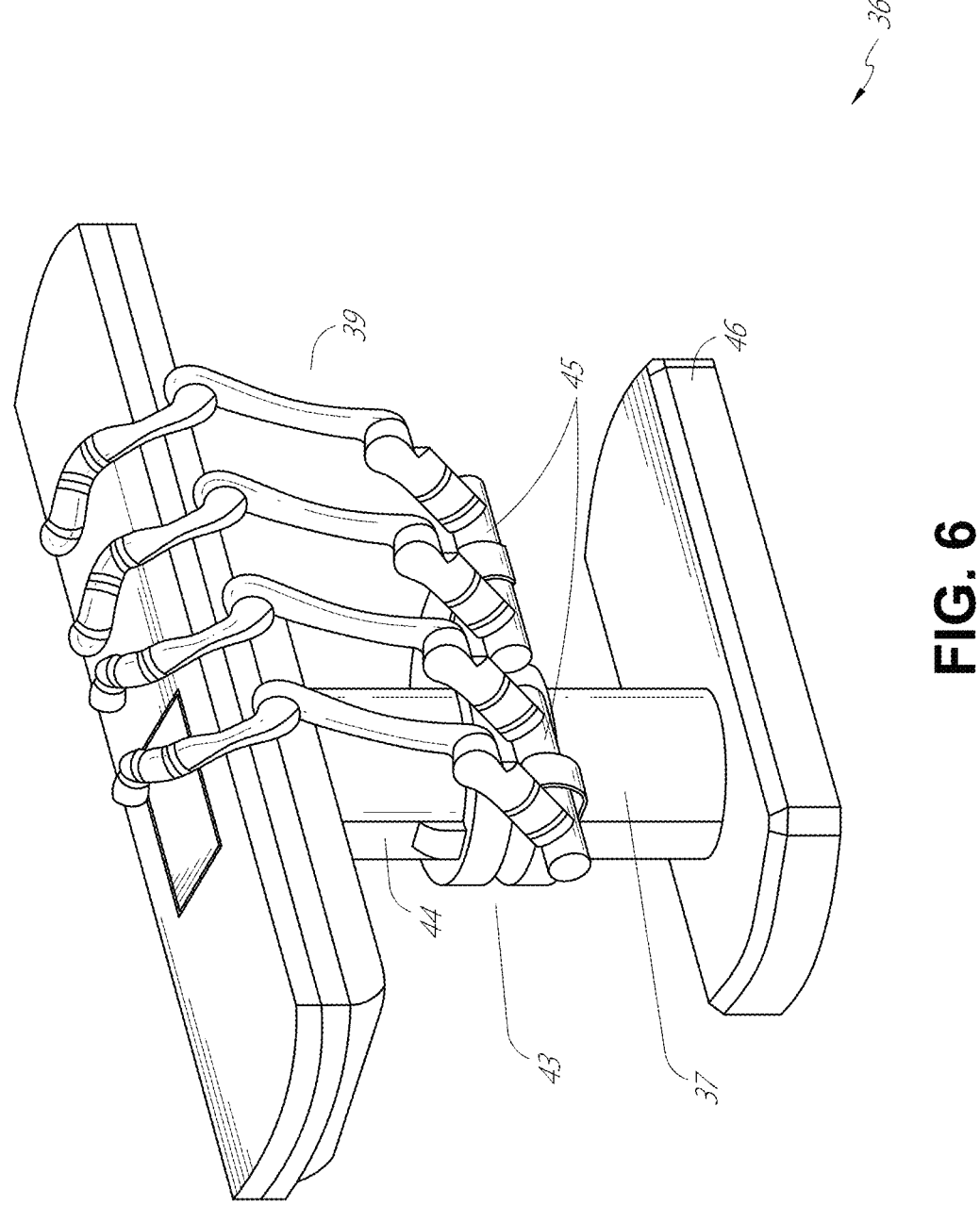
FIG. 6 provides an alternative view of the robotic system of FIG. 5.

FIG. 6 provides an alternative view of the system 36 without the patient and medical instrument for discussion purposes. As shown, the column 37 may include one or more carriages 43 shown as ring-shaped in the system 36, from which the one or more robotic arms 39 may be based. The carriages 43 may translate along a vertical column interface 44 that runs the length of the column 37 to provide different vantage points from which the robotic arms 39 may be positioned to reach the patient. The carriage(s) 43 may rotate around the column 37 using a mechanical motor positioned within the column 37 to allow the robotic arms 39 to have access to multiples sides of the table 38, such as, for example, both sides of the patient. In embodiments with multiple carriages, the carriages may be individually positioned on the column and may translate and/or rotate independently of the other carriages. While the carriages 43 need not surround the column 37 or even be circular, the ring-shape as shown facilitates rotation of the carriages 43 around the column 37 while maintaining structural balance. Rotation and translation of the carriages 43 allows the system 36 to align the medical instruments, such as endoscopes and laparoscopes, into different access points on the patient. In other embodiments (not shown), the system 36 can include a patient table or bed with adjustable arm supports in the form of bars or rails extending alongside it. One or more robotic arms 39 (e.g., via a shoulder with an elbow joint) can be attached to the adjustable arm supports, which can be vertically adjusted. By providing vertical adjustment, the robotic arms 39 are advantageously capable of being stowed compactly beneath the patient table or bed, and subsequently raised during a procedure.

Figure 9:
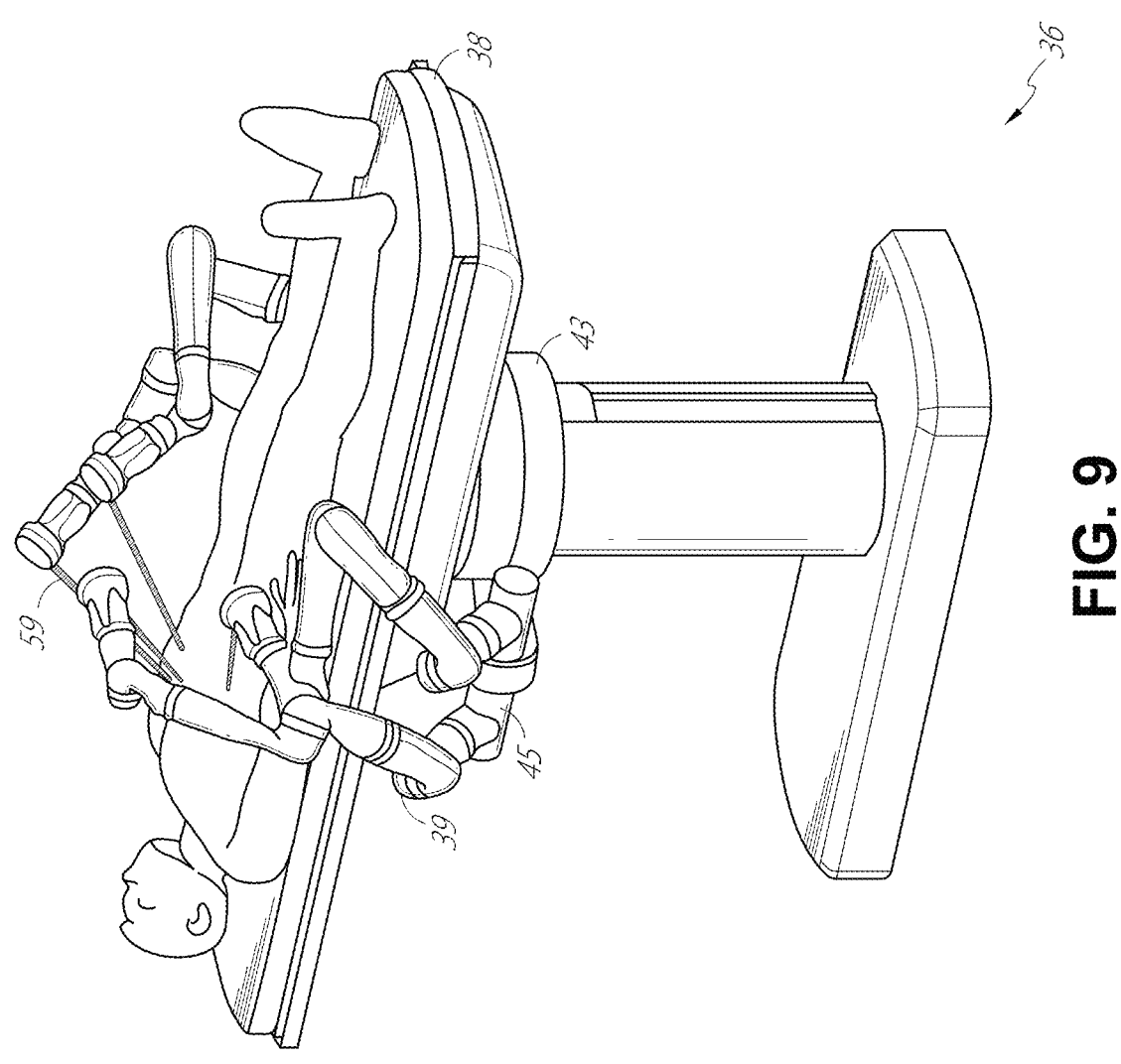
FIG. 9 illustrates an embodiment of a table-based robotic system configured for a laparoscopic procedure.

The robotic arms 39 may be mounted on the carriages 43 through a set of arm mounts 45 comprising a series of joints that may individually rotate and/or telescopically extend to provide additional configurability to the robotic arms 39. Additionally, the arm mounts 45 may be positioned on the carriages 43 such that, when the carriages 43 are appropriately rotated, the arm mounts 45 may be positioned on either the same side of the table 38 (as shown in FIG. 6), on opposite sides of the table 38 (as shown in FIG. 9), or on adjacent sides of the table 38 (not shown).

The column 37 structurally provides support for the table 38, and a path for vertical translation of the carriages 43. Internally, the column 37 may be equipped with lead screws for guiding vertical translation of the carriages, and motors to mechanize the translation of the carriages 43 based the lead screws. The column 37 may also convey power and control signals to the carriages 43 and the robotic arms 39 mounted thereon.

The table base 46 serves a similar function as the cart base 15 in the cart 11 shown in FIG. 2, housing heavier components to balance the table/bed 38, the column 37, the carriages 43, and the robotic arms 39. The table base 46 may also incorporate rigid casters to provide stability during procedures. Deployed from the bottom of the table base 46, the casters may extend in opposite directions on both sides of the base 46 and retract when the system 36 needs to be moved.

With continued reference to FIG. 6, the system 36 may also include a tower (not shown) that divides the functionality of the system 36 between the table and the tower to reduce the form factor and bulk of the table. As in earlier disclosed embodiments, the tower may provide a variety of support functionalities to the table, such as processing, computing, and control capabilities, power, fluidics, and/or optical and sensor processing. The tower may also be movable to be positioned away from the patient to improve physician access and de-clutter the operating room. Additionally, placing components in the tower allows for more storage space in the table base 46 for potential stowage of the robotic arms 39. The tower may also include a master controller or console that provides both a user interface for user input, such as keyboard and/or pendant, as well as a display screen (or touchscreen) for preoperative and intra-operative information, such as real-time imaging, navigation, and tracking information. In some embodiments, the tower may also contain holders for gas tanks to be used for insufflation.

Figure 7:
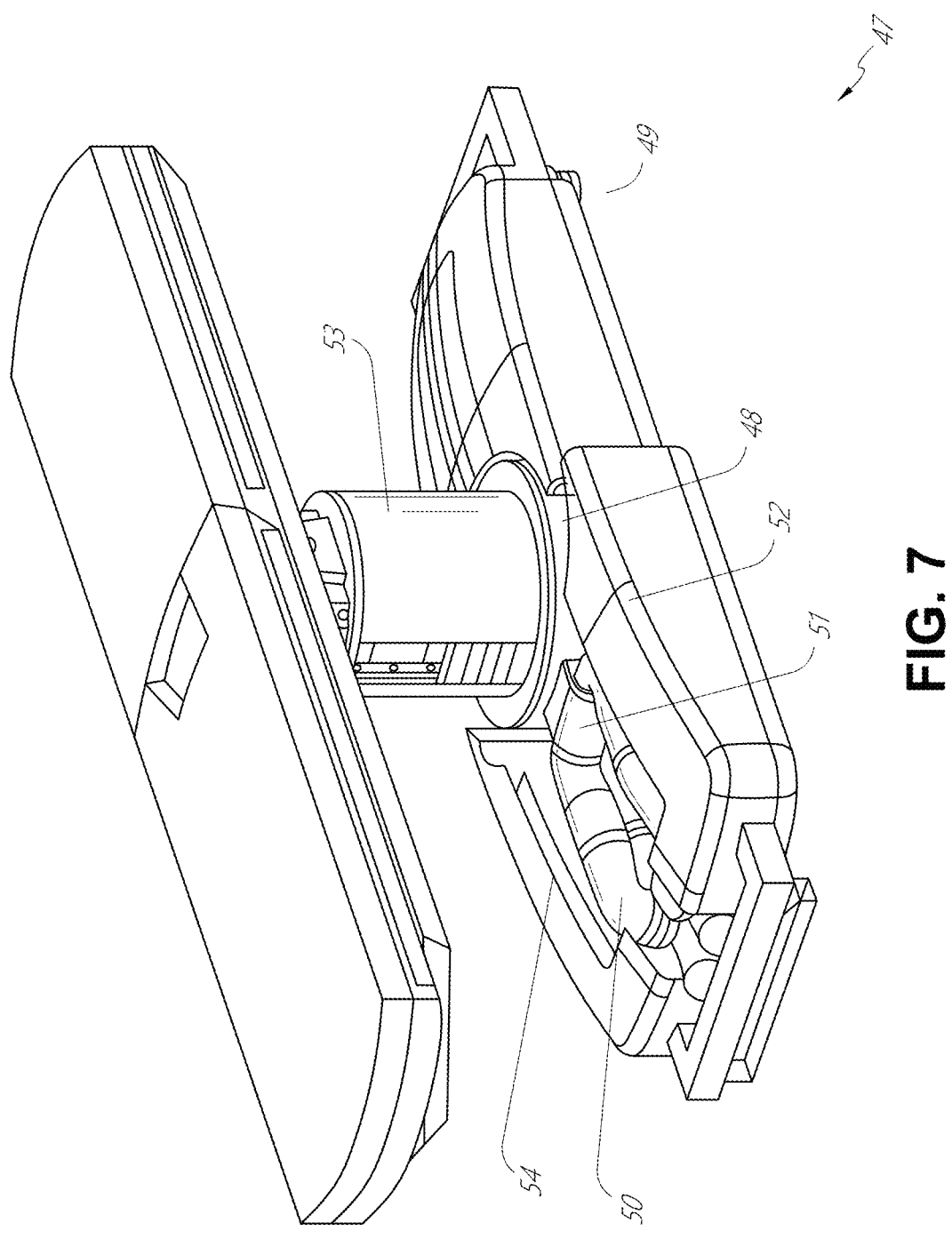
FIG. 7 illustrates an example system configured to stow robotic arm(s).

In some embodiments, a table base may stow and store the robotic arms when not in use. FIG. 7 illustrates a system 47 that stows robotic arms in an embodiment of the table-based system. In the system 47, carriages 48 may be vertically translated into base 49 to stow robotic arms 50, arm mounts 51, and the carriages 48 within the base 49. Base covers 52 may be translated and retracted open to deploy the carriages 48, arm mounts 51, and robotic arms 50 around column 53, and closed to stow to protect them when not in use. The base covers 52 may be sealed with a membrane 54 along the edges of its opening to prevent dirt and fluid ingress when closed.

Figure 8:
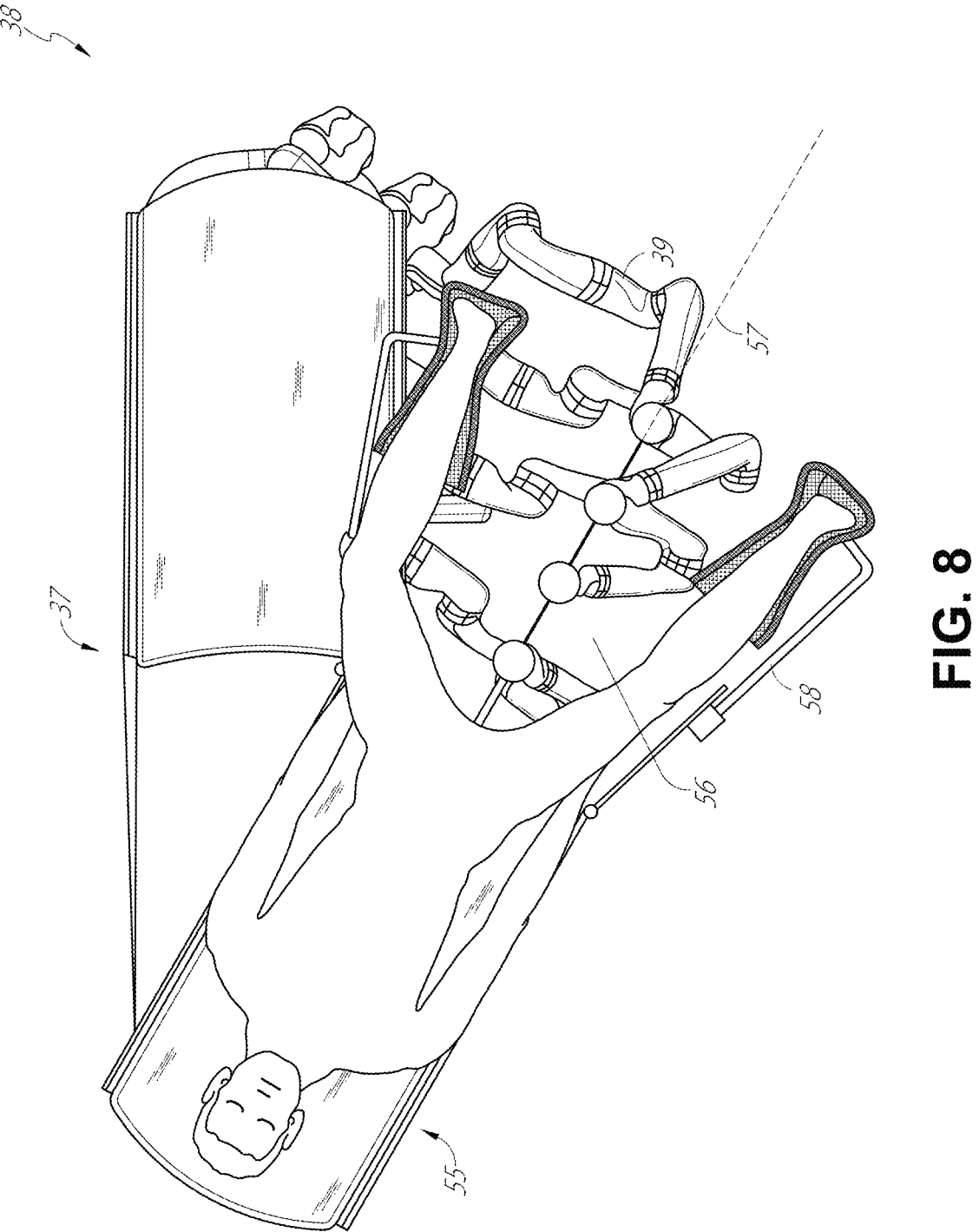
FIG. 8 illustrates an embodiment of a table-based robotic system configured for a ureteroscopic procedure.

FIG. 8 illustrates an embodiment of a robotically-enabled table-based system configured for a ureteroscopic procedure. In a ureteroscopy, the table 38 may include a swivel portion 55 for positioning a patient off-angle from the column 37 and table base 46. The swivel portion 55 may rotate or pivot around a pivot point (e.g., located below the patient's head) in order to position the bottom portion of the swivel portion 55 away from the column 37. For example, the pivoting of the swivel portion 55 allows a C-arm (not shown) to be positioned over the patient's lower abdomen without competing for space with the column (not shown) below table 38. By rotating the carriage 35 (not shown) around the column 37, the robotic arms 39 may directly insert a ureteroscope 56 along a virtual rail 57 into the patient's groin area to reach the urethra. In a ureteroscopy, stirrups 58 may also be fixed to the swivel portion 55 of the table 38 to support the position of the patient's legs during the procedure and allow clear access to the patient's groin area.

In a laparoscopic procedure, through small incision(s) in the patient's abdominal wall, minimally invasive instruments may be inserted into the patient's anatomy. In some embodiments, the minimally invasive instruments comprise an elongated rigid member, such as a shaft, which is used to access anatomy within the patient. After inflation of the patient's abdominal cavity, the instruments may be directed to perform surgical or medical tasks, such as grasping, cutting, ablating, suturing, etc. In some embodiments, the instruments can comprise a scope, such as a laparoscope. FIG. 9 illustrates an embodiment of a robotically-enabled table-based system configured for a laparoscopic procedure. As shown in FIG. 9, the carriages 43 of the system 36 may be rotated and vertically adjusted to position pairs of the robotic arms 39 on opposite sides of the table 38, such that instrument 59 may be positioned using the arm mounts 45 to be passed through minimal incisions on both sides of the patient to reach his/her abdominal cavity.

Figure 10:
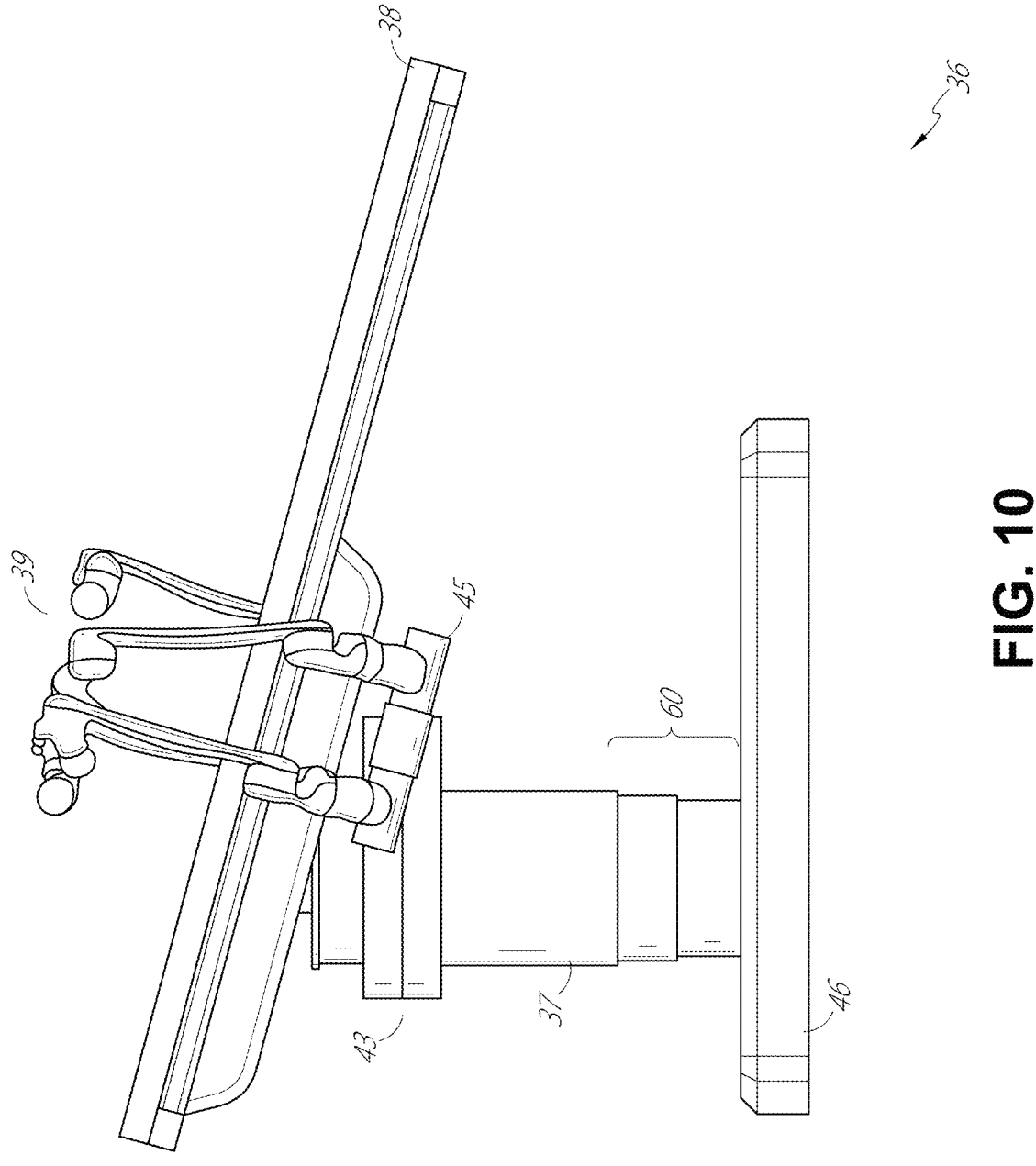
FIG. 10 illustrates an embodiment of the table-based robotic system of FIGS. 5-9 with pitch or tilt adjustment.

To accommodate laparoscopic procedures, the robotically-enabled table system may also tilt the platform to a desired angle. FIG. 10 illustrates an embodiment of the robotically-enabled medical system with pitch or tilt adjustment. As shown in FIG. 10, the system 36 may accommodate tilt of the table 38 to position one portion of the table at a greater distance from the floor than the other. Additionally, the arm mounts 45 may rotate to match the tilt such that the robotic arms 39 maintain the same planar relationship with the table 38. To accommodate steeper angles, the column 37 may also include telescoping portions 60 that allow vertical extension of the column 37 to keep the table 38 from touching the floor or colliding with the table base 46.

Figure 11:
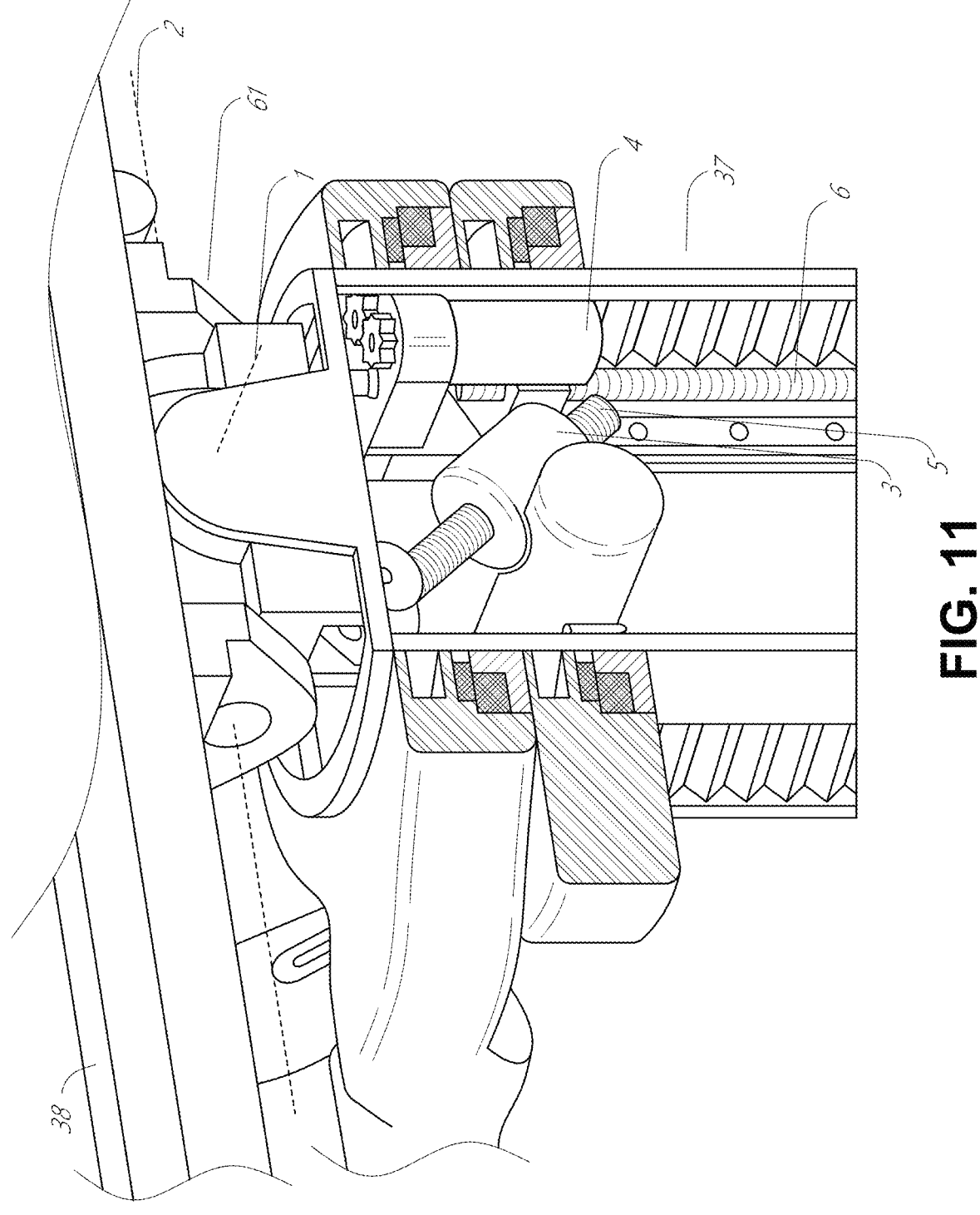
FIG. 11 provides a detailed illustration of the interface between the table and the column of the table-based robotic system of FIGS. 5-10.

FIG. 11 provides a detailed illustration of the interface between the table 38 and the column 37. Pitch rotation mechanism 61 may be configured to alter the pitch angle of the table 38 relative to the column 37 in multiple degrees of freedom. The pitch rotation mechanism 61 may be enabled by the positioning of orthogonal axes 1, 2 at the column-table interface, each axis actuated by a separate motor 3, 4 responsive to an electrical pitch angle command. Rotation along one screw 5 would enable tilt adjustments in one axis 1, while rotation along the other screw 6 would enable tilt adjustments along the other axis 2. In some embodiments, a ball joint can be used to alter the pitch angle of the table 38 relative to the column 37 in multiple degrees of freedom.

For example, pitch adjustments are particularly useful when trying to position the table in a Trendelenburg position, i.e., position the patient's lower abdomen at a higher position from the floor than the patient's upper abdomen, for lower abdominal surgery. The Trendelenburg position causes the patient's internal organs to slide towards his/her upper abdomen through the force of gravity, clearing out the abdominal cavity for minimally invasive tools to enter and perform lower abdominal surgical or medical procedures, such as laparoscopic prostatectomy.

Figure 12:
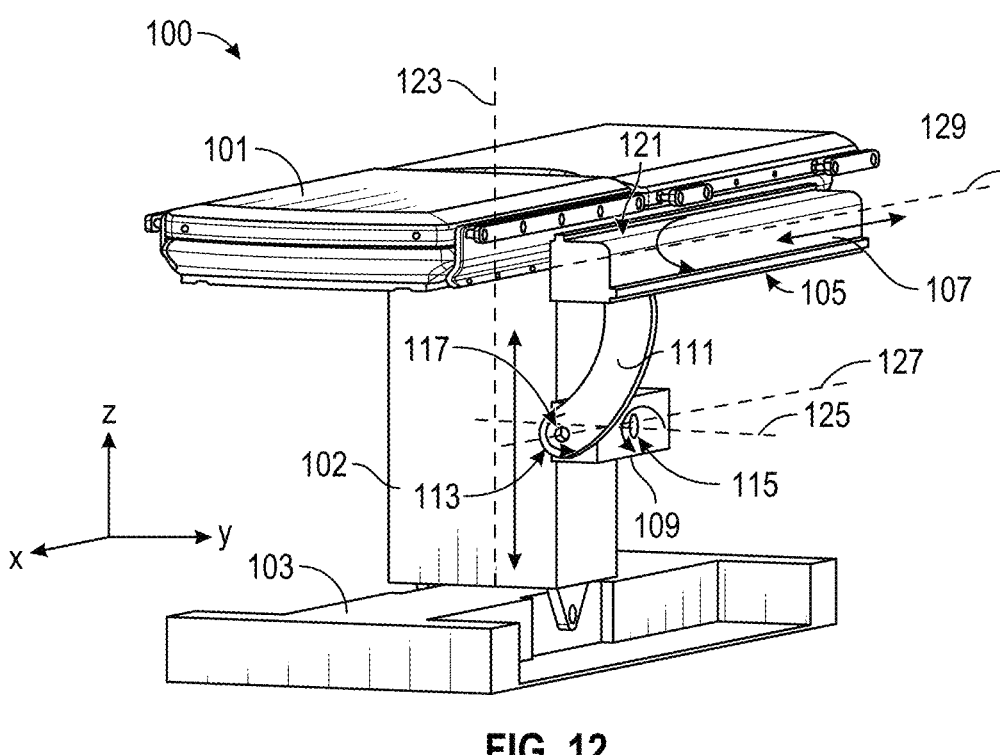
FIG. 12 illustrates an alternative embodiment of a table-based robotic system.
Figure 13:
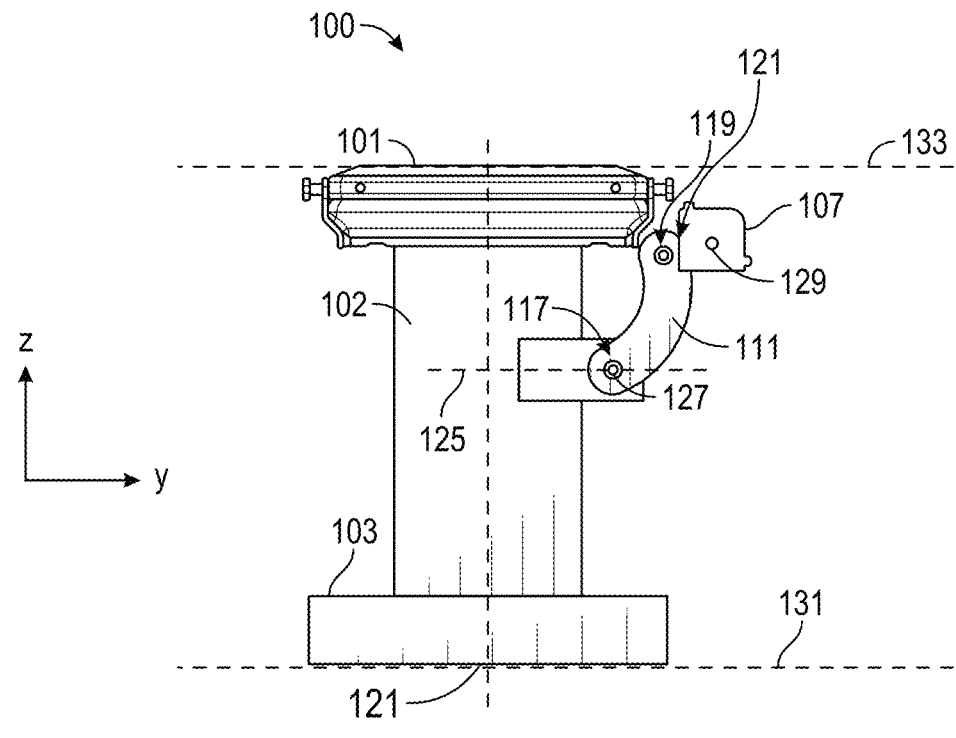
FIG. 13 illustrates an end view of the table-based robotic system of FIG. 12.

FIGS. 12 and 13 illustrate isometric and end views of an alternative embodiment of a table-based surgical robotics system 100. The surgical robotics system 100 includes one or more adjustable arm supports 105 that can be configured to support one or more robotic arms (see, for example, FIG. 14) relative to a table 101. In the illustrated embodiment, a single adjustable arm support 105 is shown, though an additional arm support can be provided on an opposite side of the table 101. The adjustable arm support 105 can be configured so that it can move relative to the table 101 to adjust and/or vary the position of the adjustable arm support 105 and/or any robotic arms mounted thereto relative to the table 101. For example, the adjustable arm support 105 may be adjusted one or more degrees of freedom relative to the table 101. The adjustable arm support 105 provides high versatility to the system 100, including the ability to easily stow the one or more adjustable arm supports 105 and any robotics arms attached thereto beneath the table 101. The adjustable arm support 105 can be elevated from the stowed position to a position below an upper surface of the table 101. In other embodiments, the adjustable arm support 105 can be elevated from the stowed position to a position above an upper surface of the table 101.

The adjustable arm support 105 can provide several degrees of freedom, including lift, lateral translation, tilt, etc. In the illustrated embodiment of FIGS. 12 and 13, the arm support 105 is configured with four degrees of freedom, which are illustrated with arrows in FIG. 12. A first degree of freedom allows for adjustment of the adjustable arm support 105 in the z-direction ("Z-lift"). For example, the adjustable arm support 105 can include a carriage 109 configured to move up or down along or relative to a column 102 supporting the table 101. A second degree of freedom can allow the adjustable arm support 105 to tilt. For example, the adjustable arm support 105 can include a rotary joint, which can allow the adjustable arm support 105 to be aligned with the bed in a Trendelenburg position. A third degree of freedom can allow the adjustable arm support 105 to "pivot up," which can be used to adjust a distance between a side of the table 101 and the adjustable arm support 105.

A fourth degree of freedom can permit translation of the adjustable arm support 105 along a longitudinal length of the table.

The surgical robotics system 100 in FIGS. 12 and 13 can comprise a table supported by a column 102 that is mounted to a base 103. The base 103 and the column 102 support the table 101 relative to a support surface. A floor axis 131 and a support axis 133 are shown in FIG. 13.

The adjustable arm support 105 can be mounted to the column 102. In other embodiments, the arm support 105 can be mounted to the table 101 or base 103. The adjustable arm support 105 can include a carriage 109, a bar or rail connector 111 and a bar or rail 107. In some embodiments, one or more robotic arms mounted to the rail 107 can translate and move relative to one another.

The carriage 109 can be attached to the column 102 by a first joint 113, which allows the carriage 109 to move relative to the column 102 (e.g., such as up and down a first or vertical axis 123). The first joint 113 can provide the first degree of freedom (Z-lift) to the adjustable arm support 105. The adjustable arm support 105 can include a second joint 115, which provides the second degree of freedom (tilt) for the adjustable arm support 105. The adjustable arm support 105 can include a third joint 117, which can provide the third degree of freedom ("pivot up") for the adjustable arm support 105. An additional joint 119 (shown in FIG. 13) can be provided that mechanically constrains the third joint 117 to maintain an orientation of the rail 107 as the rail connector 111 is rotated about a third axis 127. The adjustable arm support 105 can include a fourth joint 121, which can provide a fourth degree of freedom (translation) for the adjustable arm support 105 along a fourth axis 129.

Figure 14:
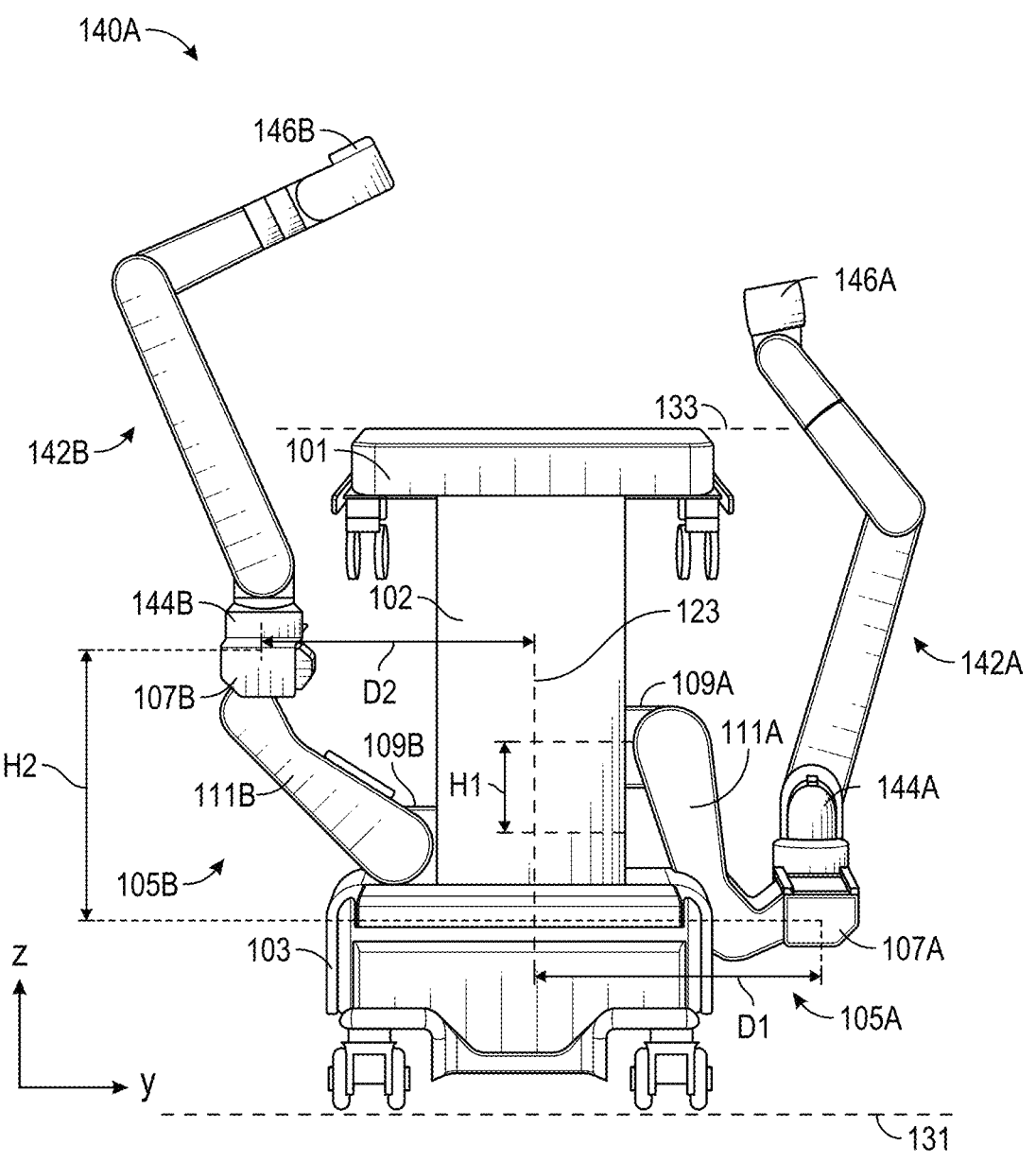
FIG. 14 illustrates an end view of a table-based robotic system with robotic arms attached thereto.

FIG. 14 illustrates an end view of the surgical robotics system 140A with two adjustable arm supports 105A, 105B mounted on opposite sides of a table 101. A first robotic arm 142A is attached to the bar or rail 107A of the first adjustable arm support 105B. The first robotic arm 142A includes a base 144A attached to the rail 107 A. The distal end of the first robotic arm 142A includes an instrument drive mechanism 146A that can attach to one or more robotic medical instruments or tools. Similarly, the second robotic arm 142B includes a base 144B attached to the rail 107B. The distal end of the second robotic arm 142B includes an instrument drive mechanism 146B. The instrument drive mechanism 146B can be configured to attach to one or more robotic medical instruments or tools.

In some embodiments, one or more of the robotic arms 142A, 142B comprises an arm with seven or more degrees of freedom. In some embodiments, one or more of the 18 robotic arms 142A, 142B can include eight degrees of freedom, including an insertion axis (1-degree of freedom including insertion), a wrist (3-degrees of freedom including wrist pitch, yaw and roll), an elbow (1-degree of freedom including elbow pitch), a shoulder (2-degrees of freedom including shoulder pitch and yaw), and base 144A, 144B (1-degree of freedom including translation). In some embodiments, the insertion degree of freedom can be provided by the robotic arm 142A, 142B, while in other embodiments, the instrument itself provides insertion via an instrument-based insertion architecture.

C. Instrument Driver & Interface.

The end effectors of the system's robotic arms may comprise (i) an instrument driver (alternatively referred to as "instrument drive mechanism" or "instrument device manipulator") that incorporates electro-mechanical means for actuating the medical instrument and (ii) a removable or detachable medical instrument, which may be devoid of any electromechanical components, such as motors. This dichotomy may be driven by the need to sterilize medical instruments used in medical procedures, and the inability to adequately sterilize expensive capital equipment due to their intricate mechanical assemblies and sensitive electronics. Accordingly, the medical instruments may be designed to be detached, removed, and interchanged from the instrument driver (and thus the system) for individual sterilization or disposal by the physician or the physician's staff. In contrast, the instrument drivers need not be changed or sterilized, and may be draped for protection.

FIG. 15 illustrates an example instrument driver. Positioned at the distal end of a robotic arm, instrument driver 62 comprises one or more drive units 63 arranged with parallel axes to provide controlled torque to a medical instrument via drive shafts 64. Each drive unit 63 comprises an individual drive shaft 64 for interacting with the instrument, a gear head 65 for converting the motor shaft rotation to a desired torque, a motor 66 for generating the drive torque, an encoder 67 to measure the speed of the motor shaft and provide feedback to the control circuitry, and control circuitry 68 for receiving control signals and actuating the drive unit. Each drive unit 63 being independently controlled and motorized, the instrument driver 62 may provide multiple (e.g., four as shown in FIG. 15) independent drive outputs to the medical instrument. In operation, the control circuitry 68 would receive a control signal, transmit a motor signal to the motor 66, compare the resulting motor speed as measured by the encoder 67 with the desired speed, and modulate the motor signal to generate the desired torque.

For procedures that require a sterile environment, the robotic system may incorporate a drive interface, such as a sterile adapter connected to a sterile drape, that sits between the instrument driver and the medical instrument. The chief purpose of the sterile adapter is to transfer angular motion from the drive shafts of the instrument driver to the drive inputs of the instrument while maintaining physical separation, and thus sterility, between the drive shafts and drive inputs. Accordingly, an example sterile adapter may comprise a series of rotational inputs and outputs intended to be mated with the drive shafts of the instrument driver and drive inputs on the instrument. Connected to the sterile adapter, the sterile drape, comprised of a thin, flexible material such as transparent or translucent plastic, is designed to cover the capital equipment, such as the instrument driver, robotic arm, and cart (in a cart-based system) or table (in a table-based system). Use of the drape would allow the capital equipment to be positioned proximate to the patient while still being located in an area not requiring sterilization (i.e., non-sterile field). On the other side of the sterile drape, the medical instrument may interface with the patient in an area requiring sterilization (i.e., sterile field).

D. Medical Instrument.

Figure 16:
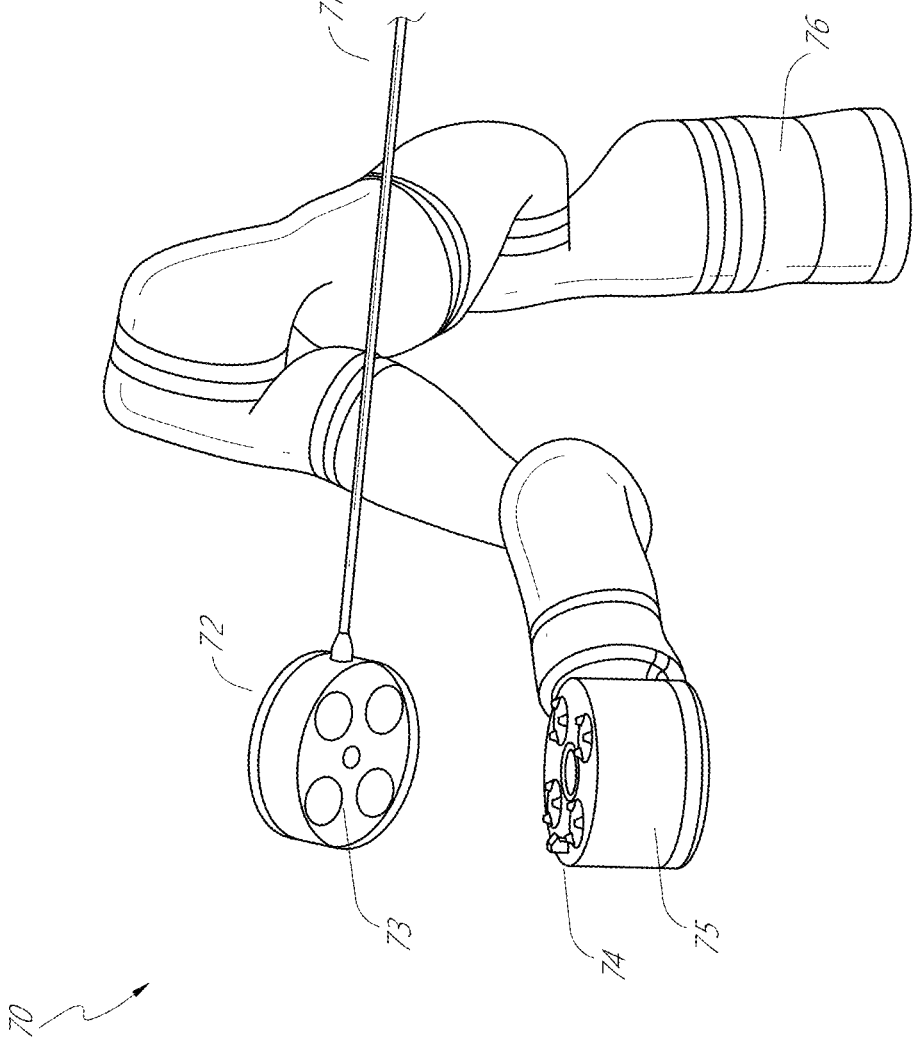
FIG. 16 illustrates an exemplary medical instrument with a paired instrument driver.

FIG. 16 illustrates an example medical instrument with a paired instrument driver. Like other instruments designed for use with a robotic system, medical instrument 70 comprises an elongated shaft 71 (or elongate body) and an instrument base 72. The instrument base 72, also referred to as an "instrument handle" due to its intended design for manual interaction by the physician, may generally comprise rotatable drive inputs 73, e.g., receptacles, pulleys or spools, that are designed to be mated with drive outputs 74 that extend through a drive interface on instrument driver 75 at the distal end of robotic arm 76. When physically connected, latched, and/or coupled, the mated drive inputs 73 of the instrument base 72 may share axes of rotation with the drive outputs 74 in the instrument driver 75 to allow the transfer of torque from the drive outputs 74 to the drive inputs 73. In some embodiments, the drive outputs 74 may comprise splines that are designed to mate with receptacles on the drive inputs 73.

The elongated shaft 71 is designed to be delivered through either an anatomical opening or lumen, e.g., as in endoscopy, or a minimally invasive incision, e.g., as in laparoscopy. The elongated shaft 71 may be either flexible (e.g., having properties similar to an endoscope) or rigid (e.g., having properties similar to a laparoscope) or contain a customized combination of both flexible and rigid portions. When designed for laparoscopy, the distal end of a rigid elongated shaft may be connected to an end effector extending from a jointed wrist formed from a clevis with at least one degree of freedom and a surgical tool or medical instrument, such as, for example, a grasper or scissors, that may be actuated based on force from the tendons as the drive inputs rotate in response to torque received from the drive outputs 74 of the instrument driver 75. When designed for endoscopy, the distal end of a flexible elongated shaft may include a steerable or controllable bending section that may be articulated and bent based on torque received from the drive outputs 74 of the instrument driver 75.

Torque from the instrument driver 75 is transmitted down the elongated shaft 71 using tendons along the elongated shaft 71. These individual tendons, such as pull wires, may be individually anchored to individual drive inputs 73 within the instrument handle 72. From the handle 72, the tendons are directed down one or more pull lumens along the elongated shaft 71 and anchored at the distal portion of the elongated shaft 71, or in the wrist at the distal portion of the elongated shaft. During a surgical procedure, such as a laparoscopic, endoscopic or hybrid procedure, these tendons may be coupled to a distally mounted end effector, such as a wrist, grasper, or scissor. Under such an arrangement, torque exerted on drive inputs 73 would transfer tension to the tendon, thereby causing the end effector to actuate in some way. In some embodiments, during a surgical procedure, the tendon may cause a joint to rotate about an axis, thereby causing the end effector to move in one direction or another. Alternatively, the tendon may be connected to one or more jaws of a grasper at the distal end of the elongated shaft 71, where tension from the tendon causes the grasper to close.

In endoscopy, the tendons may be coupled to a bending or articulating section positioned along the elongated shaft 71 (e.g., at the distal end) via adhesive, control ring, or other mechanical fixation. When fixedly attached to the distal end of a bending section, torque exerted on the drive inputs 73 would be transmitted down the tendons, causing the softer, bending section (sometimes referred to as the articulable section or region) to bend or articulate. Along the non-bending sections, it may be advantageous to spiral or helix the individual pull lumens that direct the individual tendons along (or inside) the walls of the endoscope shaft to balance the radial forces that result from tension in the pull wires. The angle of the spiraling and/or spacing therebetween may be altered or engineered for specific purposes, wherein tighter spiraling exhibits lesser shaft compression under load forces, while lower amounts of spiraling results in greater shaft compression under load forces, but limits bending. On the other end of the spectrum, the pull lumens may be directed parallel to the longitudinal axis of the elongated shaft 71 to allow for controlled articulation in the desired bending or articulable sections.

In endoscopy, the elongated shaft 71 houses a number of components to assist with the robotic procedure. The shaft

71 may comprise a working channel for deploying surgical tools (or medical instruments), irrigation, and/or aspiration to the operative region at the distal end of the shaft 71. The shaft 71 may also accommodate wires and/or optical fibers to transfer signals to/from an optical assembly at the distal tip, which may include an optical camera. The shaft 71 may also accommodate optical fibers to carry light from proximally-located light sources, such as light emitting diodes, to the distal end of the shaft 71.

At the distal end of the instrument 70, the distal tip may also comprise the opening of a working channel for delivering tools for diagnostic and/or therapy, irrigation, and aspiration to an operative site. The distal tip may also include a port for a camera, such as a fiberscope or a digital camera, to capture images of an internal anatomical space. Relatedly, the distal tip may also include ports for light sources for illuminating the anatomical space when using the camera.

In the example of FIG. 16, the drive shaft axes, and thus the drive input axes, are orthogonal to the axis of the elongated shaft 71. This arrangement, however, complicates roll capabilities for the elongated shaft 71. Rolling the elongated shaft 71 along its axis while keeping the drive inputs 73 static results in undesirable tangling of the tendons as they extend off the drive inputs 73 and enter pull lumens within the elongated shaft 71. The resulting entanglement of such tendons may disrupt any control algorithms intended to predict movement of the flexible elongated shaft 71 during an endoscopic procedure.

Figure 17:
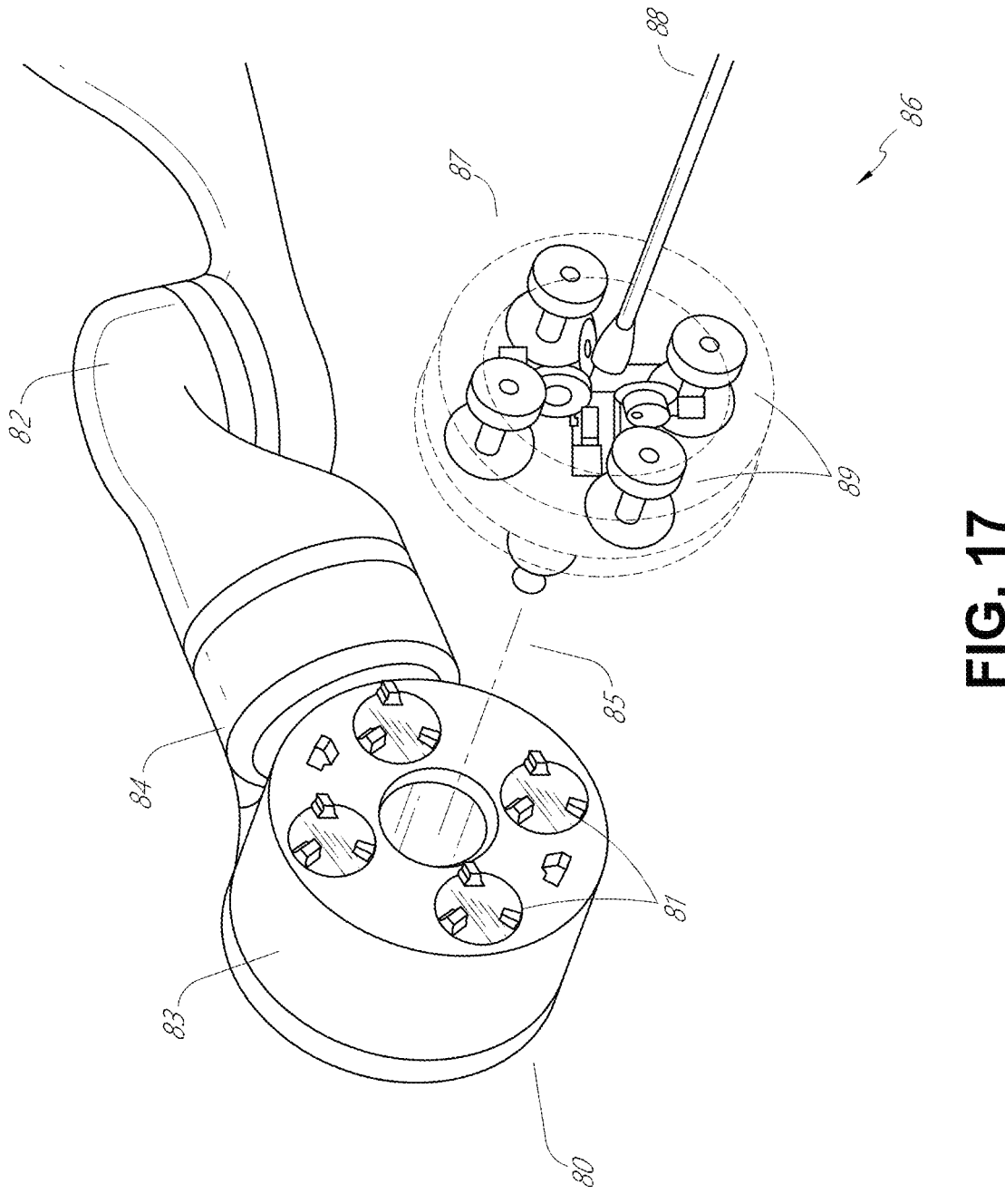
FIG. 17 illustrates an alternative design for an instrument driver and instrument where the axes of the drive units are parallel to the axis of the elongated shaft of the instrument.

FIG. 17 illustrates an alternative design for an instrument driver and instrument where the axes of the drive units are parallel to the axis of the elongated shaft of the instrument. As shown, a circular instrument driver 80 comprises four drive units with their drive outputs 81 aligned in parallel at the end of a robotic arm 82. The drive units, and their respective drive outputs 81, are housed in a rotational assembly 83 of the instrument driver 80 that is driven by one of the drive units within the assembly 83. In response to torque provided by the rotational drive unit, the rotational assembly 83 rotates along a circular bearing that connects the rotational assembly 83 to the non-rotational portion 84 of the instrument driver 80. Power and controls signals may be communicated from the non-rotational portion 84 of the instrument driver 80 to the rotational assembly 83 through electrical contacts that may be maintained through rotation by a brushed slip ring connection (not shown). In other embodiments, the rotational assembly 83 may be responsive to a separate drive unit that is integrated into the nonrotatable portion 84, and thus not in parallel to the other drive units. The rotational mechanism 83 allows the instrument driver 80 to rotate the drive units, and their respective drive outputs 81, as a single unit around an instrument driver axis 85.

Like earlier disclosed embodiments, an instrument 86 may comprise an elongated shaft portion 88 and an instrument base 87 (shown with a transparent external skin for discussion purposes) comprising a plurality of drive inputs 89 (such as receptacles, pulleys, and spools) that are configured to receive the drive outputs 81 in the instrument driver 80. Unlike prior disclosed embodiments, the instrument shaft 88 extends from the center of the instrument base 87 with an axis substantially parallel to the axes of the drive inputs 89, rather than orthogonal as in the design of FIG. 16.

When coupled to the rotational assembly 83 of the instrument driver 80, the medical instrument 86, comprising instrument base 87 and instrument shaft 88, rotates in combination with the rotational assembly 83 about the instrument driver axis 85. Since the instrument shaft 88 is positioned at the center of instrument base 87, the instrument shaft 88 is coaxial with instrument driver axis 85 when attached. Thus, rotation of the rotational assembly 83 causes the instrument shaft 88 to rotate about its own longitudinal axis. Moreover, as the instrument base 87 rotates with the instrument shaft 88, any tendons connected to the drive inputs 89 in the instrument base 87 are not tangled during rotation. Accordingly, the parallelism of the axes of the drive outputs 81, drive inputs 89, and instrument shaft 88 allows for the shaft rotation without tangling any control tendons.

Figure 18:
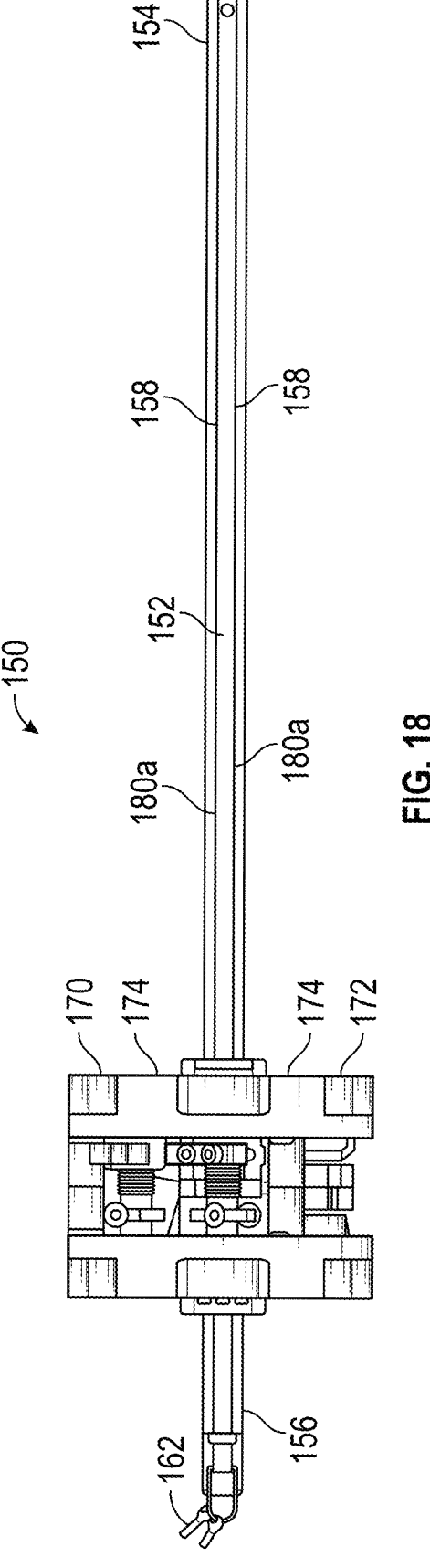
FIG. 18 illustrates an instrument having an instrument-based insertion architecture.

FIG. 18 illustrates an instrument having an instrument based insertion architecture in accordance with some embodiments. The instrument 150 can be coupled to any of the instrument drivers discussed above. The instrument 150 comprises an elongated shaft 152, an end effector 162 connected to the shaft 152, and a handle 170 coupled to the shaft 152. The elongated shaft 152 comprises a tubular member having a proximal portion 154 and a distal portion 156. The elongated shaft 152 comprises one or more channels or grooves 158 along its outer surface. The grooves 158 are configured to receive one or more wires or cables 180 therethrough. One or more cables 180 thus run along an outer surface of the elongated shaft 152. In other embodiments, cables 180 can also run through the elongated shaft 152. Manipulation of the one or more cables 180 (e.g., via an instrument driver) results in actuation of the end effector 162.

The instrument handle 170, which may also be referred to as an instrument base, may generally comprise an attachment interface 172 having one or more mechanical inputs 174, e.g., receptacles, pulleys or spools, that are designed to be reciprocally mated with one or more torque couplers on an attachment surface of an instrument driver. In some embodiments, the instrument 150 comprises a series of pulleys or cables that enable the elongated shaft 152 to translate relative to the handle 170. In other words, the instrument 150 itself comprises an instrument-based insertion architecture that accommodates insertion of the instrument, thereby minimizing the reliance on a robot arm to provide insertion of the instrument 150. In other embodiments, a robotic arm can be largely responsible for instrument insertion.

E. Controller.

Any of the robotic systems described herein can include an input device or controller for manipulating an instrument attached to a robotic arm. In some embodiments, the controller can be coupled (e.g., communicatively, electronically, electrically, wirelessly and/or mechanically) with an instrument such that manipulation of the controller causes a corresponding manipulation of the instrument e.g., via master slave control.

Figure 19:
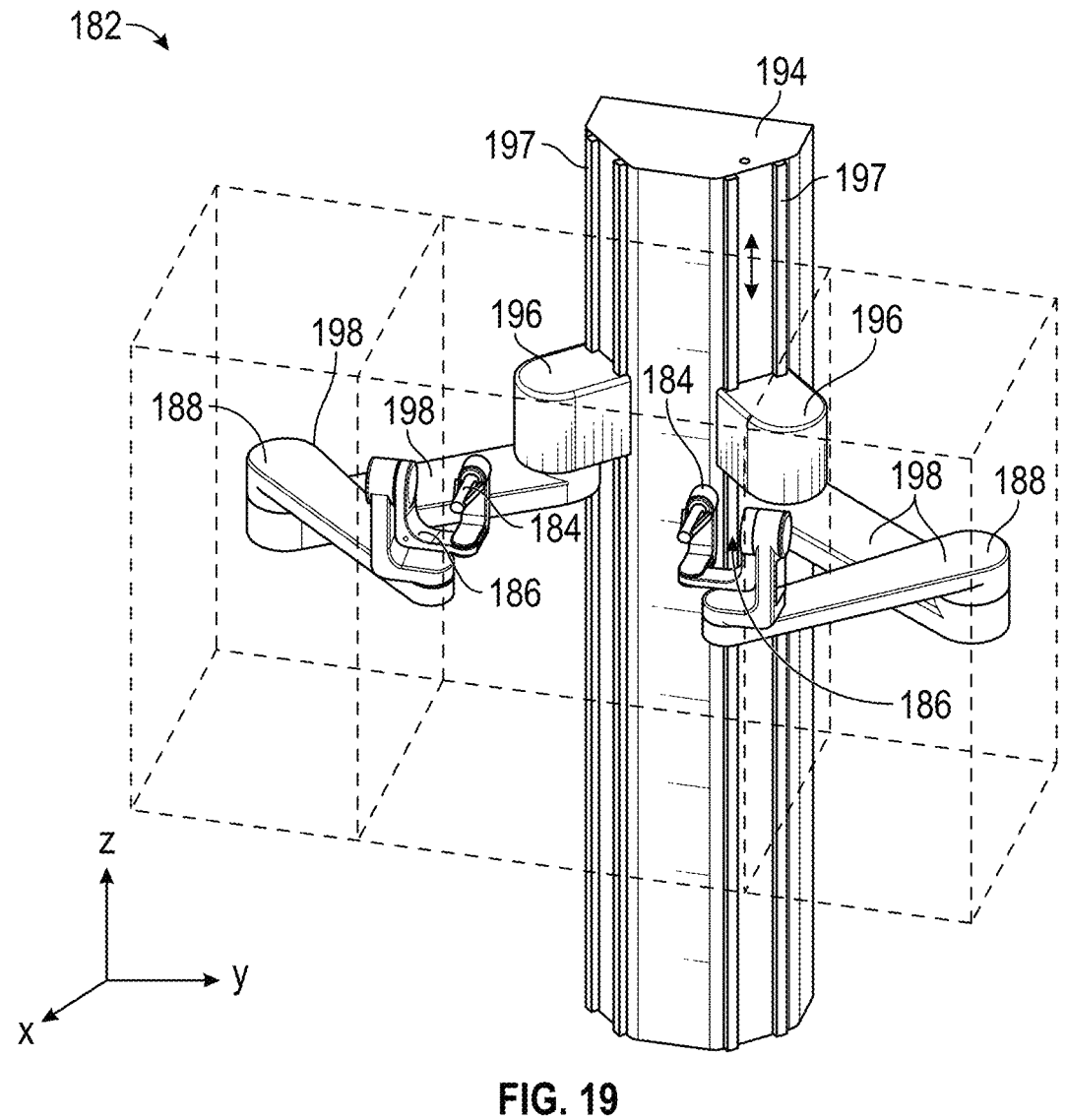
FIG. 19 illustrates an exemplary controller.

FIG. 19 is a perspective view of an embodiment of a controller 182. In the present embodiment, the controller 182 comprises a hybrid controller that can have both impedance and admittance control. In other embodiments, the controller 182 can utilize just impedance or passive control. In other embodiments, the controller 182 can utilize just admittance control. By being a hybrid controller, the controller 182 advantageously can have a lower perceived inertia while in use.

In the illustrated embodiment, the controller 182 is configured to allow manipulation of two medical instruments, and includes two handles 184. Each of the handles 184 is connected to a gimbal 186. Each gimbal 186 is connected to a positioning platform 188.

As shown in FIG. 19, each positioning platform 188 includes a SCARA arm (selective compliance assembly robot arm) 198 coupled to a column 194 by a prismatic joint 196. The prismatic joints 196 are configured to translate along the column 194 (e.g., along rails 197) to allow each of the handles 184 to be translated in the z-direction, providing a first degree of freedom. The SCARA arm 198 is configured to allow motion of the handle 184 in an x-y plane, providing two additional degrees of freedom.

In some embodiments, one or more load cells are positioned in the controller. For example, in some embodiments, a load cell (not shown) is positioned in the body of each of the gimbals 186. By providing a load cell, portions of the controller 182 are capable of operating under admittance control, thereby advantageously reducing the perceived inertia of the controller while in use. In some embodiments, the positioning platform 188 is configured for admittance control, while the gimbal 186 is configured for impedance control. In other embodiments, the gimbal 186 is configured for admittance control, while the positioning platform 188 is configured for impedance control. Accordingly, for some embodiments, the translational or positional degrees of freedom of the positioning platform 188 can rely on admittance control, while the rotational degrees of freedom of the gimbal 186 rely on impedance control.

F. Navigation and Control.

Traditional endoscopy may involve the use of fluoroscopy (e.g., as may be delivered through a C-arm) and other forms of radiation-based imaging modalities to provide endoluminal guidance to an operator physician. In contrast, the robotic systems contemplated by this disclosure can provide for non-radiation-based navigational and localization means to reduce physician exposure to radiation and reduce the amount of equipment within the operating room. As used herein, the term "localization" may refer to determining and/or monitoring the position of objects in a reference coordinate system. Technologies such as preoperative mapping, computer vision, real-time EM tracking, and robot command data may be used individually or in combination to achieve a radiation-free operating environment. In other cases, where radiation-based imaging modalities are still used, the preoperative mapping, computer vision, real-time EM tracking, and robot command data may be used individually or in combination to improve upon the information obtained solely through radiation-based imaging modalities.

Figure 20:
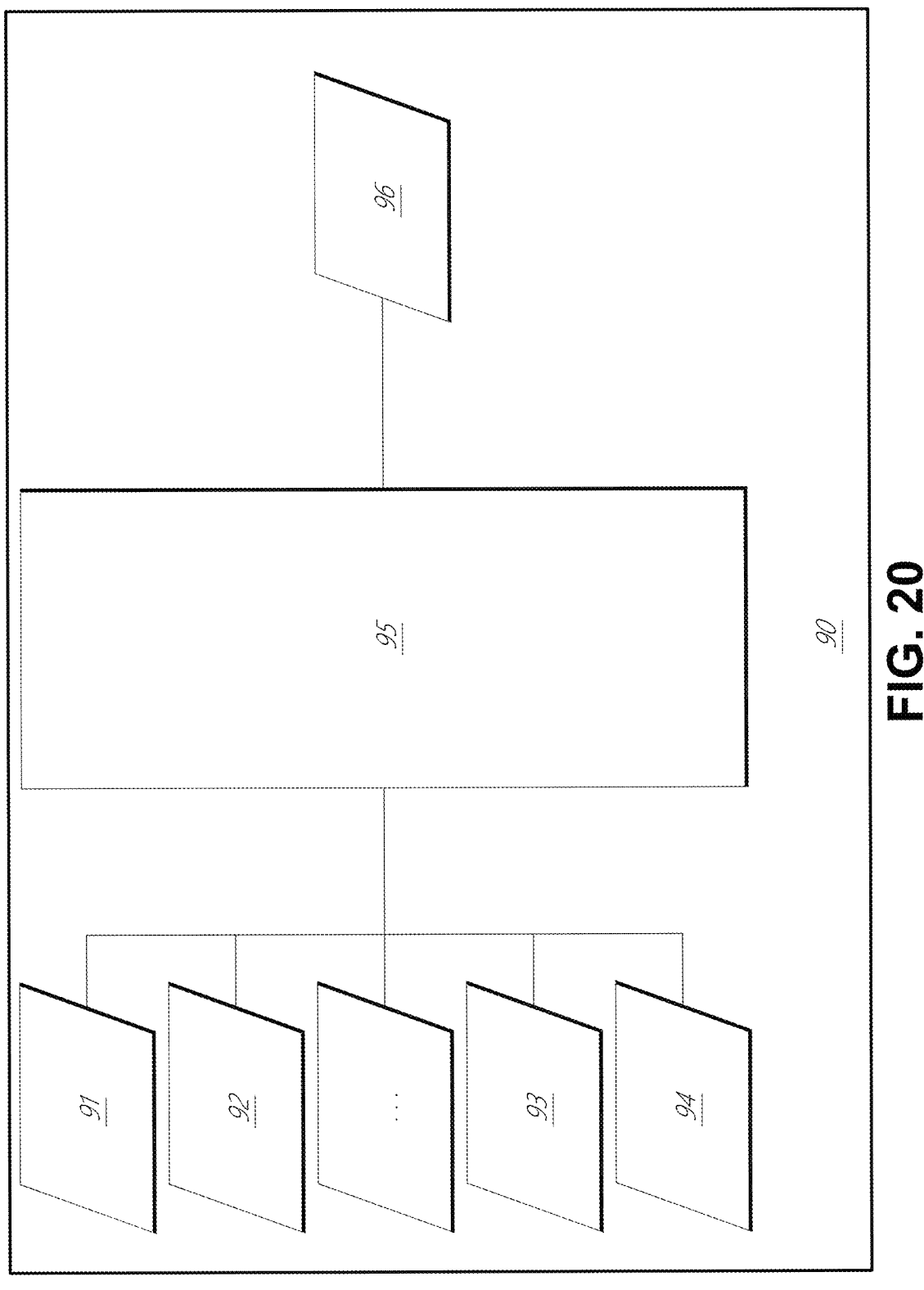
FIG. 20 depicts a block diagram illustrating a localization system that estimates a location of one or more elements of the robotic systems of FIGS. 1-10, such as the location of the instrument of FIGS. 16-18, in accordance to an example embodiment.

FIG. 20 is a block diagram illustrating a localization system 90 that estimates a location of one or more elements of the robotic system, such as the location of the instrument, in accordance to an example embodiment. The localization system 90 may be a set of one or more computer devices configured to execute one or more instructions. The computer devices may be embodied by a processor (or processors) and computer-readable memory in one or more components discussed above. By way of example and not limitation, the computer devices may be in the tower 30 shown in FIG. 1, the cart 11 shown in FIGS. 1-4, the beds shown in FIGS. 5-14, etc.

As shown in FIG. 20, the localization system 90 may include a localization module 95 that processes input data 91-94 to generate location data 96 for the distal tip of a medical instrument. The location data 96 may be data or logic that represents a location and/or orientation of the distal end of the instrument relative to a frame of reference. The frame of reference can be a frame of reference relative to the anatomy of the patient or to a known object, such as an EM field generator (see discussion below for the EM field generator).

The various input data 91-94 are now described in greater detail. Preoperative mapping may be accomplished through the use of the collection of low dose CT scans. Preoperative CT scans are reconstructed into three-dimensional images, which are visualized, e.g. as "slices" of a cutaway view of the patient's internal anatomy. When analyzed in the aggregate, image-based models for anatomical cavities, spaces and structures of the patient's anatomy, such as a patient lung network, may be generated. Techniques such as center-line geometry may be determined and approximated from the CT images to develop a three-dimensional volume of the patient's anatomy, referred to as model data 91 (also referred to as "preoperative model data" when generated using only preoperative CT scans). The use of center-line geometry is discussed in U.S. patent application Ser. No. 14/523,760, issued as U.S. Pat. No. 9,763,741 on Sep. 19, 2017, the contents of which are herein incorporated in its entirety. Network topological models may also be derived from the CT-images, and are particularly appropriate for bronchoscopy.

In some embodiments, the instrument may be equipped with a camera to provide vision data (or image data) 92. The localization module 95 may process the vision data 92 to enable one or more vision-based (or image-based) location tracking modules or features. For example, the preoperative model data 91 may be used in conjunction with the vision data 92 to enable computer vision-based tracking of the medical instrument (e.g., an endoscope or an instrument advance through a working channel of the endoscope). For example, using the preoperative model data 91, the robotic system may generate a library of expected endoscopic images from the model based on the expected path of travel of the endoscope, each image linked to a location within the model. Intraoperatively, this library may be referenced by the robotic system in order to compare real-time images captured at the camera (e.g., a camera at a distal end of the endoscope) to those in the image library to assist localization.

Other computer vision-based tracking techniques use feature tracking to determine motion of the camera, and thus the endoscope. Some features of the localization module 95 may identify circular geometries in the preoperative model data 91 that correspond to anatomical lumens and track the change of those geometries to determine which anatomical lumen was selected, as well as the relative rotational and/or translational motion of the camera. Use of a topological map may further enhance vision-based algorithms or techniques.

Optical flow, another computer vision-based technique, may analyze the displacement and translation of image pixels in a video sequence in the vision data 92 to infer camera movement. Examples of optical flow techniques may include motion detection, object segmentation calculations, luminance, motion compensated encoding, stereo disparity measurement, etc. Through the comparison of multiple frames over multiple iterations, movement and location of the camera (and thus the endoscope) may be determined.

The localization module 95 may use real-time EM tracking to generate a real-time location of the endoscope in a global coordinate system that may be registered to the patient's anatomy, represented by the preoperative model. In EM tracking, an EM sensor (or tracker) comprising one or more sensor coils embedded in one or more locations and orientations in a medical instrument (e.g., an endoscopic tool) measures the variation in the EM field created by one or more static EM field generators positioned at a known location. The location information detected by the EM sensors is stored as EM data 93. The EM field generator (or transmitter), may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. These distances and orientations may be intraoperatively "registered" to the patient anatomy (e.g., the preoperative model) in order to determine the geometric transformation that aligns a single location in the coordinate system with a position in the preoperative model of the patient's anatomy. Once registered, an embedded EM tracker in one or more positions of the medical instrument (e.g., the distal tip of an endoscope) may provide real-time indications of the progression of the medical instrument through the patient's anatomy.

Robotic command and kinematics data 94 may also be used by the localization module 95 to provide localization data 96 for the robotic system. Device pitch and yaw resulting from articulation commands may be determined during preoperative calibration. Intraoperatively, these calibration measurements may be used in combination with known insertion depth information to estimate the position of the instrument. Alternatively, these calculations may be analyzed in combination with EM, vision, and/or topological modeling to estimate the position of the medical instrument within the network.

As FIG. 20 shows, a number of other input data can be used by the localization module 95. For example, although not shown in FIG. 20, an instrument utilizing shape-sensing fiber can provide shape data that the localization module 95 can use to determine the location and shape of the instrument.

The localization module 95 may use the input data 91-94 in combination(s). In some cases, such a combination may use a probabilistic approach where the localization module 95 assigns a confidence weight to the location determined from each of the input data 91-94. Thus, where the EM data may not be reliable (as may be the case where there is EM interference) the confidence of the location determined by the EM data 93 can be decrease and the localization module 95 may rely more heavily on the vision data 92 and/or the robotic command and kinematics data 94.

As discussed above, the robotic systems discussed herein may be designed to incorporate a combination of one or more of the technologies above. The robotic system's computer-based control system, based in the tower, bed and/or cart, may store computer program instructions, for example, within a non-transitory computer-readable storage medium such as a persistent magnetic storage drive, solid state drive, or the like, that, upon execution, cause the system to receive and analyze sensor data and user commands, generate control signals throughout the system, and display the navigational and localization data, such as the position of the instrument within the global coordinate system, anatomical map, etc.

2. Foot Pedal Assemblies with Dynamic Visual Indicators

Robotic medical systems, such as those described above with reference to FIGS. 1-20 and others, can include foot pedal assemblies with visual indicators. Features and functionality of the visual indicators will be described in this section with reference to the example embodiments illustrated in FIGS. 21-30. The illustrated embodiments are provided by way of example and illustration and are not intended to be limiting. Upon consideration of this disclosure, one of skill in the art will appreciate that other configurations and embodiments, which are within the scope of this disclosure for foot pedal assemblies with dynamic visual indicators are possible. Further, several notable advantages of the foot pedal assemblies with dynamic visual indicators configured for use with robotic medical systems will be described below. Not all of the described advantages need be provided by every embodiment, and the foot pedal assemblies with dynamic visual indicators may also provide advantages that are not described herein.

As described above, robotic medical systems can include one or more robotic components configured to perform robotic medical procedures. Such robotic components can include, for example, one or more robotic arms, one or more robotic instrument drive mechanisms or instrument manipulators, and/or one or more robotic medical instruments as described previously. Robotic systems can also include a user console that is configured to allow a user, such as a physician or surgeon, to provide inputs for controlling the robotic system. For example, the user console can be configured to allow the user to control the one or more robotic arms, the one or more robotic instrument drive mechanisms or instrument manipulators, and/or the one or more robotic medical instruments of the robotic system. In some embodiments, the user console may be configured to allow the user to provide control inputs in a variety of ways. For example, the user console can include handheld inputs configured to be operated with the user's hands as well as additional inputs configured to be operated by the user's feet.

Figure 21:
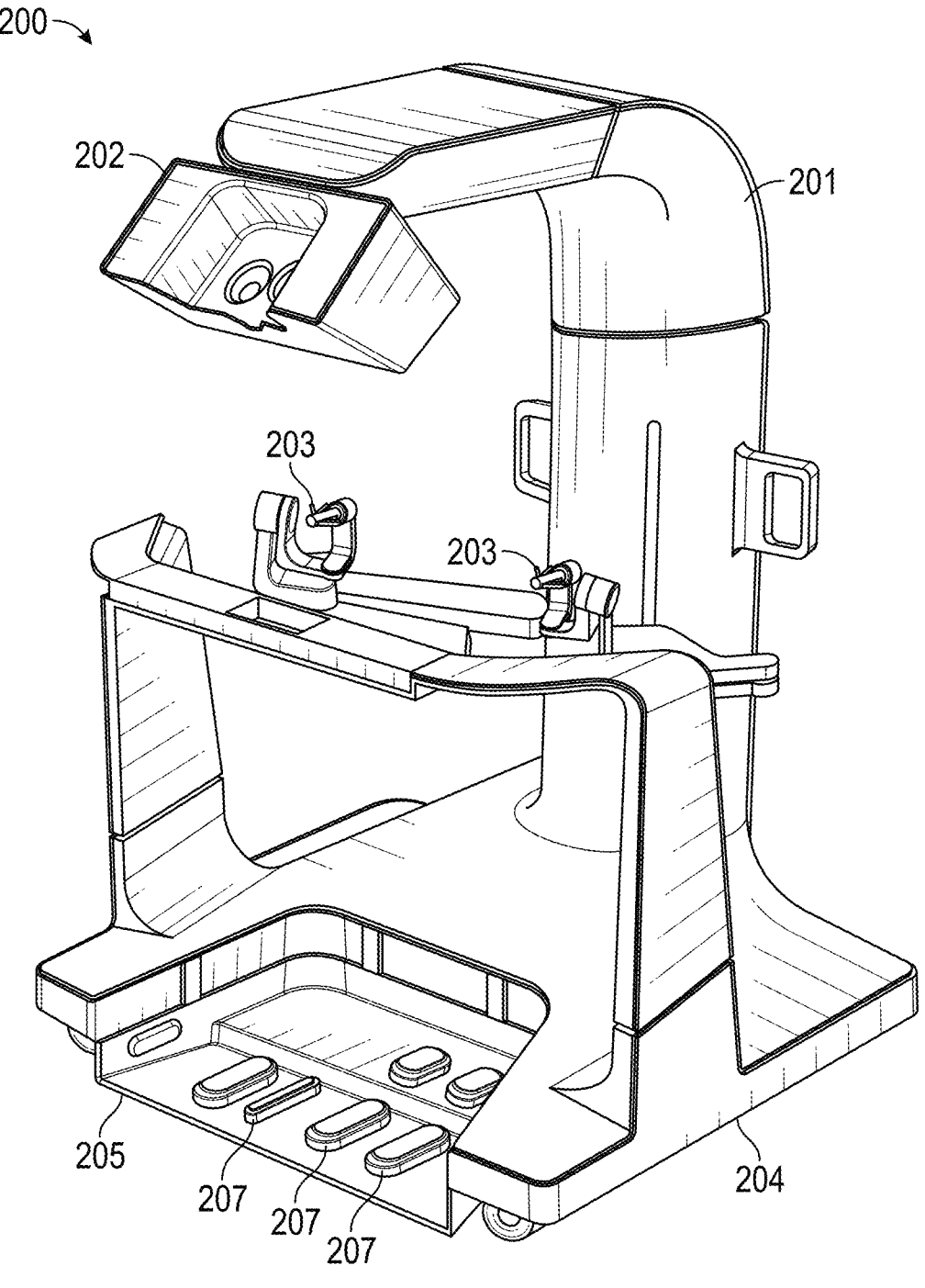
FIG. 21 illustrates a perspective view of an embodiment of a user console for a robotic medical system including a viewer, controllers, and a pedal assembly.

FIG. 21 is a perspective view illustrating an embodiment of a user console 200 configured for use with robotic medical systems such as those described above with reference to FIGS. 1-20 and others. The user console 200 can be configured to allow the user to provide inputs for controlling the robotic medical system and to allow the user to view images from one or more cameras associated with the robotic medical system in order to facilitate control thereof. In the illustrated embodiment, the user console 200 comprises a housing 201 including a base 204, a viewer 202, one or more hand-operated controllers 203 (also referred to as master controllers), and a foot pedal assembly 205 including a plurality of foot pedals 207.

The housing 201 can be provided to support and orient the various components of the user console 200 such that they can be operated by the user. In preferred embodiments, the housing 201 positions the components, such as the viewer 202, master controllers 203, and foot pedal assembly 205, such that a user can access and operate each of these simultaneously or independently while maintaining an ergonomic body position. Various configurations for the housing 201 are possible. In the illustrated embodiment, the housing 201 of the user console 200 also includes a base 204. The base 204 can be configured to support the user console 200. In some embodiments, the base 204 is configured to be supported by the ground. The base 204 may also include one or more wheels and/or other structures that configured the user console 200 to be moveable.

The viewer 202 of the user console 200 can be configured to allow the user to view images from one or more cameras or other imaging devices of or associated with the robotic medical system in order to facilitate control of the system to perform a robotic medical procedure. As described above, one or more components of the robotic system can include one or more imaging devices, such as one or more cameras. For example, a robotically-controllable endoscope of the robotic medical system can include a camera positioned at a distal tip thereof. The user can view an image from the camera of the endoscope in the viewer 202 in order to facilitate control of the endoscope and/or other components of the robotic medical system. As another example, the robotic system may include one or more cameras laparoscopically inserted into a patient. The user can view images from the laparoscopically inserted cameras in order to facilitate control of one or more additional robotically controlled medical instruments, such as one or more additional laparoscopically inserted medical instruments. The viewer 202 can comprise a screen for viewing the images from the one or more cameras. In some embodiments, the viewer 202 comprises a stereographic or stereoscopic viewer. In some embodiments, the viewer 202 may allow the user to view an output from other imagining devices, such as medical imagers like fluoroscopic images, and/or computer models of the patient's anatomy.

The viewer 202 can be positioned on the housing 201 such that the user can view the viewer 202 when seated in front of the user console 200. In some embodiments, the housing 201 is configured such that the user inserts his or her head into the viewer 202 in order to block out ambient light such that the images in the viewer 202 can be more easily seen. This, however, need not be the case in all embodiments, and other arrangements for the viewer 202 on the user console 200 are also possible.

The one or more hand-operated controllers 203 are configured to be operated with the user's hands in order to provide control of various aspects or components of the robotic medical system. In the illustrated embodiment, the controllers 203 comprise two inputs, each input configured to be gripped and operated with one of the user's hands. Examples of such controllers 203 have been described above with reference to FIG. 19. In some embodiments, the controllers 203 can be selectively coupled to robotic medical instruments of the robotic system in a master-slave configuration, such that movement of the controllers 203 causes a corresponding movement of the coupled robotic medical instrument as described above. Thus, by manipulating the controllers 203, the user can control a corresponding manipulation of the robotic medical instruments. Accordingly, in some embodiments, the controllers 203 can be referred to as a master controller of the system.

As the robotic medical system can include more robotic medical instruments than controllers 203, the controllers 203 can be selectively coupled to medical instruments as desired by the user to facilitate the procedure. For example, a controller 203 can be selectively coupled to a laparoscopic camera to allow the user to control and position the laparoscopic camera so as to provide a view of one or more additional laparoscopic tools within a treatment site of the patient. The user can then selectively couple the controllers 203 to the one or more additional laparoscopic tools in order to control them directly. Additional features and functionality of the controllers 203 have been described above with reference to FIG. 19, which illustrates one embodiment thereof. Other embodiments of handheld controllers 203 are also possible, including controllers that include keyboards, touchpads, buttons, joysticks, mice, etc.

In the illustrated embodiment, the user console 200 also includes the foot pedal assembly 205, which can include one or more pedals 207 that are positioned so as to be operable by a user's feet. As shown in FIG. 21, the foot pedal assembly 205 can be integrated into the base 204 of the housing 201 of the user console 200. In some embodiments, however, the pedal assembly 205 is not integrated into the housing 201. For example, the pedal assembly 205 can comprise a discrete component configured to be positioned at the user's feet in order to provide foot-based inputs. In this case, the pedal assembly can be moveable independently from the housing 201 of the user console 200. The pedal assembly 205 and the pedals 207 can provide an additional physical user interface that is typically (though not always) configured to be supplemental to the hand-operated controllers 203. For example, the pedals 207 of the pedal assembly 205 can be configured to control various aspects of the robotic medical system and components thereof.

Figure 22:
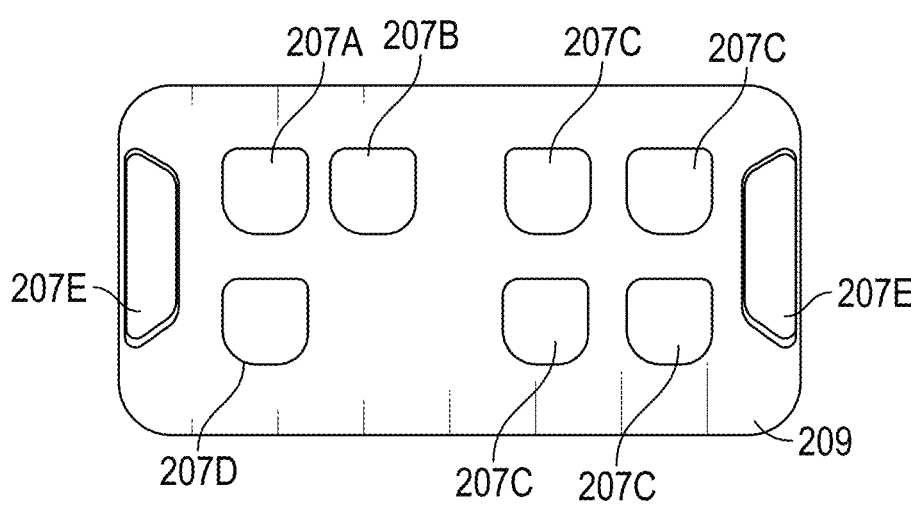
FIG. 22 illustrates a top view of an embodiment of a pedal assembly including a plurality of pedals configured to control different functions of a robotic medical system.

FIG. 22 illustrates a top view of an example embodiment of a foot pedal assembly 205, including an arrangement of pedals 207. With reference to FIG. 22, certain functionality of the foot pedal assembly 205 will be described. However, the specific configuration and arrangement of the pedals 207 on the pedal assembly 205 as illustrated in FIG. 22 is not intended to be limiting. For example, in some embodiments, the pedals 207 can be provided with a different arrangement, including a different number of total pedals 207 (e.g., a greater or fewer number of pedals 207 than shown in the illustrated embodiment) as well as different placement positions for the pedals 207. Further, although certain pedals 207 are described below as having certain functionality, other pedals 207 in other locations can provide the described functionality or different functionality in other embodiments. Additionally, in some embodiments, functionality described as associated with the pedals 207 can be provided by other inputs, such as controllers 203 or other inputs on the console 200.

As shown in the illustrated embodiment, the pedal assembly 205 comprises a plurality of pedals 207 positioned on a base component or pedal board 209. In the illustrated embodiment, the pedal assembly comprises a workspace adjustment pedal 207A. The workspace adjustment pedal 207 A can be configured as a "clutch" pedal. While a user is controlling a left instrument and a right instrument using the controllers 203, the user may reach a non-ergonomic position. To readjust the control of the left instrument and the right instrument, the user may wish to decouple the controllers 203 from the instruments temporarily. The workspace adjustment pedal 207 A can be configured to provide this functionality. When actuated, the workspace adjustment pedal 207 A can decouple the controllers 203 from the instruments such that the position of the controllers 203 can be readjusted without causing a corresponding movement at the instruments. When the workspace adjustment pedal 207 A is released, the controllers 203 can be recoupled to the instruments such that the controllers 203 can be used for further control of the instruments.

In the illustrated embodiment, the pedal assembly 205 can include a spare pedal 207B. In some embodiments, a user can assign a desired functionality to the spare pedal 207B as desired.

The pedal assembly 205 can include left and right instrument pedals 207C for controlling functionality of the active instruments of the robotic medical system. The active instruments can be those instruments to which the controllers 203 are currently coupled in a master-slave configuration. The left and right instrument pedals 207C can be configured to perform or activate different functions of the instruments (e.g., cut, grasp, coagulate, etc.). In the illustrated embodiment, the left and right instrument pedals 207C comprise two pedals provided for the left active instruments (aligned vertically) and two pedals provided for the right active instruments (aligned vertically). Other arrangements are also possible. By providing a pair of pedals for each of the left active instrument and right active instrument, this may allow a user to control different modalities for each instrument. For example, a user controlling a vessel sealer via the left hand controller 203 can use the bottom left instrument pedal 207C to perform a cut function and the top left instrument pedal 207C to perform a coagulation function.

As illustrated, the pedal assembly 205 can include a camera pedal 207D. The camera pedal 207D can be used to control a camera of the robotic medical system. For example, rather than using the controllers 203 to drive (e.g., control) one or more instruments, a user may desire to drive the camera using the controllers 203. In some embodiments, by pressing on the camera pedal 207D, one or more of the controllers 203 can be coupled to a robotic camera such that the controllers 203 can be used to control the camera. This can allow a user to quickly and simply readjust the position or view of the camera by pressing the camera pedal 207D and moving the controllers to adjust the camera. When the camera pedal 207D is released, the controllers 203 can be recoupled to the left and right instruments.

The pedal assembly 205 can also include swap pedals 207E. The swap pedals 207E can be configured to allow a user to swap which robotic instruments are currently coupled to the controllers 203. In the illustrated embodiment, the swap pedals 207E are located on the lateral edges of pedal board 209. This may facilitate intuitive use of the swap pedals 207E. For example, in some embodiments, a robotic system can include more than two robotic medical instruments. One of the instruments can be coupled to the right controller 203, and the other of the instruments can be coupled to the left controller 203. By pressing the right swap pedal 207E, the user can change which instrument is currently coupled to the right controller 203, and by pressing the left swap pedal 207E, the user can change which instrument is currently coupled to the left controller 203. Further, in some embodiments, the swap pedals 207E can configured such that they are pressed laterally (e.g., with an outside of the users foot). Other configurations are also possible.

As described above, a robotic medical system can include a plurality of robotic components that can be controlled with the user console 200 using the controllers 203 and pedal assembly 205. In many surgical procedures, the operating room can be very dark. As such, it can be challenging to safely and effectively use the pedal assembly 205, as it can be difficult for users to know where each pedal is and its associated function. As robotic systems that rely on foot pedals become increasingly complex (e.g., with an increased number of robotic arms and robotic medical instruments), correct identification of foot pedals 207 by a user is important for safe and effective use of the robotic systems. As will be described in more detail below, this disclosure provides for dynamic indicators on foot pedal assemblies 205 and other structures to facilitate identification and use of the pedals 207 on the foot pedal assembly 205.

Often times, it can be a challenge to identify and utilize the correct pedals in an operating room, which can be dimly lit. To facilitate identification and use of the pedals 207 of the foot pedal assembly 205, the foot pedal assembly 205 can advantageously include dynamic indicators positioned thereon. In some embodiments, the dynamic indicators can be visual indicators (such as lights, screens, or other displays) that can communicate information to a user. The indicators are referred to herein as "dynamic" because, in some embodiments, the indicators can change based on a variety of factors, including, for example, a user input, a state of the robotic system, a state of a component of the robotic system (such as a state of a robotic arm, a state of a robotic medical instrument, etc.), and/or a type of medical procedure being performed, among other factors. In some embodiments, the system is configured to determine a state of the robotic system and adjust the dynamic indicators of the foot pedal assembly 205 accordingly based on the determined state. Thus, in certain situations, the dynamic indicators on the foot pedal assembly 205 may display in one way, and in different situations, the dynamic indicators on the foot pedal assembly 205 may display in a different way. This can offer improved functionality and control over previous systems, which have generally relied on wholly static indicators (such permanent labels or etchings) in order to identify pedal functionality.

Use of dynamic indicators can also facilitate use of a single pedal 207 of the foot pedal assembly 205 for performing multiple functions. For example, a pedal 207 can initially be associated with a particular function of a medical instrument and the same pedal 207 can later be associated with a different function of the same medical instrument, a different function of a different medical instrument, or a different function of another aspect of the robotic medical system. Advantageously, the dynamic indicators described herein can update based on the particular function currently assigned to the pedal 207 to provide a clearer indication of the pedal functionality. In contrast, such updates with wholly static indicators are not possible, making it disadvantageous to use such indicators in complex robotic systems. Due to the dynamic nature of the visual indicators described herein, they can be turned on and off, swapped between the different pedals 207, and/or controlled by a user to suit the particular context of the system at that moment in time.

As mentioned above, in some embodiments, the dynamic indicators can comprise visual indicators. Visual indicators can be, for example, in the form of direct lighting, up-lighting, back-lighting, LED panels, screens, or any combination thereof. In some embodiments, the visual indicators can be configured to change patterns (e.g., a blinking pattern) and/or change intensity or brightness. In some embodiments, the dynamic indicators can be used to indicate when an associated foot pedal has changed from one state to another (e.g., from a first state to a second state or from a non-operational state to an operational state). The indicators can be associated with each pedal, as shown in FIG. 23A, or with the foot pedal assembly as a whole, as shown in FIG. 23B.

Figure 23A:
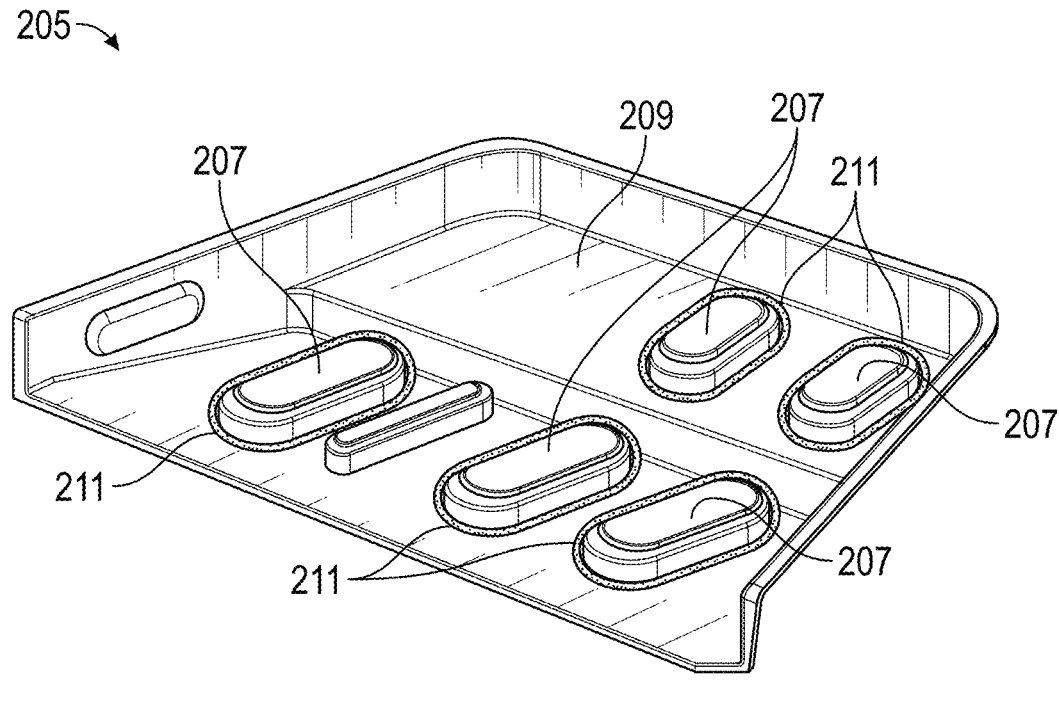
FIG. 23A is a perspective view of an embodiment of a pedal assembly including a plurality of dynamic visual indicators associated with pedals thereof.

FIG. 23A illustrates an embodiment of a foot pedal assembly 205 in which dynamic indicators 211 configured as lights are associated with individual pedals 207 of the foot pedal assembly 205. In the illustrated embodiment, the indicators 211 are configured as perimeter or ring lights that surround the pedals 207. Each pedal 207 can be surrounded by one or more indicators 211. In some embodiments, all pedals 207 have a corresponding indicator 211, although this need not be the case in all embodiments. For example, in some embodiments, some pedals 207 are not associated with any indicator 211 or different numbers of indicators 211.

Although the illustrated embodiment includes indicators 211 configured as ring lights that surround each pedal 207, other configurations are also possible. For example, indicators 211 can be configured as visual indicators (e.g., lights) positioned on any surface of the pedals 207 (such as the upper or side surfaces of the pedals 207). Additionally or alternatively, indicators 211 can be configured as visual indicators on surfaces of the pedal board 209. Indicators 211 can be positioned on the pedal board 209 at locations associated with the pedal 207 to which they correspond. For example, indicators 211 can be positioned on the pedal board 209 in front of, behind, or to the lateral sides of the associated pedal 209. In the figures, a region of shading around the pedals 207 is representative of the indicator 211 itself or an area of illumination provided by the indicator 211. In some instances in the figures, different shading or cross-hatching has been used to illustrate different indicators that can be provided by the indicators 211 (e.g., indications of different colors).

Figure 23B:
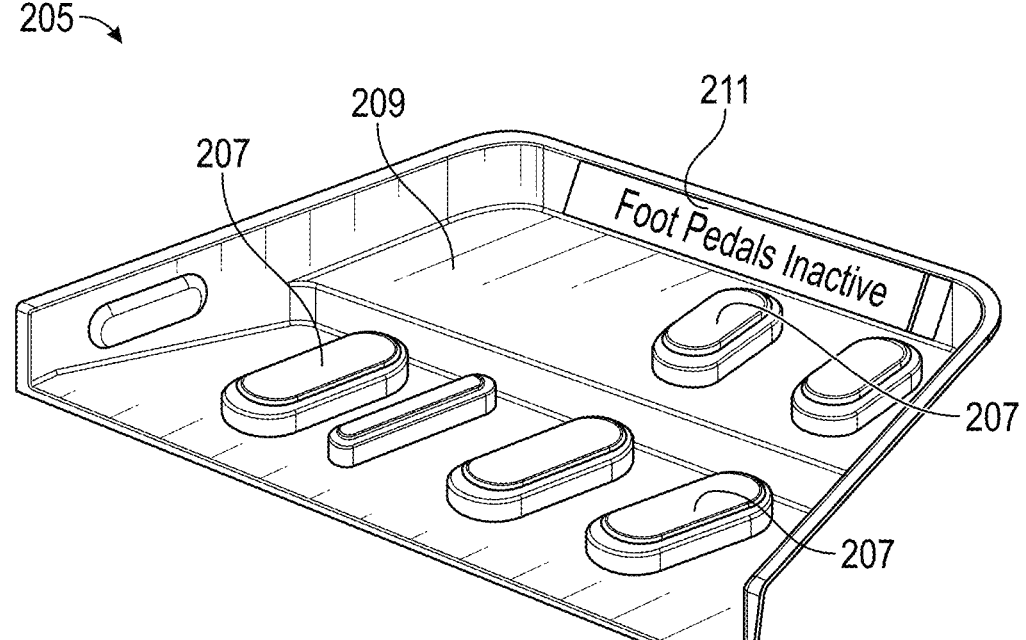
FIG. 23B is a perspective view of an embodiment of a pedal assembly including a display-type dynamic visual indicator.

FIG. 23B illustrates another example of a pedal assembly 205 that includes an indicator 211 configured as a display or screen for displaying text or other symbols. In the illustrated embodiment, the indicator 211 is positioned on a rear wall of the pedal board 209, although other locations for the indicator 211 are also possible. For example, the indicator 211 is configured as a screen that can be positioned on any surface of the pedal board 211 and/or on the pedals 207 themselves. Further, although only one indicator 211 configured as a screen is shown in the illustrated embodiment of FIG. 23B, other numbers of screen-type indicators 211 are also possible. For example, in an embodiment, a screen-type indicator 211 can be provided for each pedal 207 of the pedal assembly 205. The indicator 211 configured as a screen can be configured to update and display information contextually based on a variety of factors related to the robotic system as described throughout this section.

FIGS. 23A and 23B provide examples of visual indicators 211 (e.g., light-based indicators 211 in FIG. 23A and display or screen indicators 211 in FIG. 23B). In some embodiments, the dynamic indicators 211 can be non-visual indicators. For example, in some embodiments, the foot pedals 207 can be associated with haptic feedback indicators (e.g., in the form of vibrations) that can inform a surgeon of a state of the foot pedal. In some embodiments, the foot pedals can be associated with sounds that are derived from or provided by the foot pedal system.

As mentioned above, the indicators 211 can be configured to display information or otherwise provide indications that are determined based on various factors. FIGS. 24A-24C and FIGS. 25A-25C illustrate multiple examples of indications that can be provided with the indicators 211. In FIGS. 24A-24C the indicator 211 is provided as a "constant" indicator. As used in this example, a "constant" indicator 211 is one that constantly associates a particular pedal 207 with a particular indication, such as a particular color of lighting. In the embodiment illustrated in FIGS. 24A-24C, the lower right pedal 207 is backlit with a first color (e.g., yellow as represented by the cross-hatching in figures) in a number of scenarios. For example, FIG. 24A illustrates that the indicator 211 associated with the lower right pedal 207 can be lit with the first color when a monopolar instrument is ready for activation with that pedal 207. FIG. 24B illustrates that the indicator 211 associated with the lower right pedal 207 can be lit with the first color when the instrument is removed (e.g., decoupled from a robotic arm). And FIG. 24C illustrates that the indicator 211 associated with the lower right pedal 207 can be lit with the first color when a stapling instrument is installed and ready for activation by the pedal 207.

Thus, in these examples, the indicator 211 can be referred to as a constant indicator because the indicator 211 provides a constant indication for a variety of functions that can be provided by the pedal 207 depending on the context of the system. For example, in FIG. 24A, the context of the system 200 can be that a monopolar instrument of the system is in a ready state for activation. Based on this context, the indicator 211 associated with the lower right pedal 207 can be lit with the first color. In the example of FIG. 24B, the context of the system can be that the instrument has been unloaded. Based on this context, the indicator 211 can be lit with the first color. And, in the example of FIG. 24C, the context of the system can be that a stapler instrument of the system is in a ready state for activation. Based on this context, the indicator 211 can be lit with the first color. Accordingly, in each of FIGS. 24A-24C the indicator 211 provides a constant indication as illustrated by the constant cross-hatching in the figures.

Providing a constant indication with the indicator 211 can beneficially help a user of the system easily identify a particular pedal 207 of the pedal assembly 205. For example, when the indicator 211 is a constant indicator, a constant indication of lighting a pedal 207 with a first color allows the user to easily and consistently identify the pedal 207. Further, although described as "constant" in FIGS. 24A-24C, the indicator 211 can still be considered a dynamic indicator because it can still be configured to provide other indications (e.g., indications in other colors) in other contexts. This can provide improved functionality over truly static indicators, such as those provided by static labels applied to the pedals.

Figure 25A:
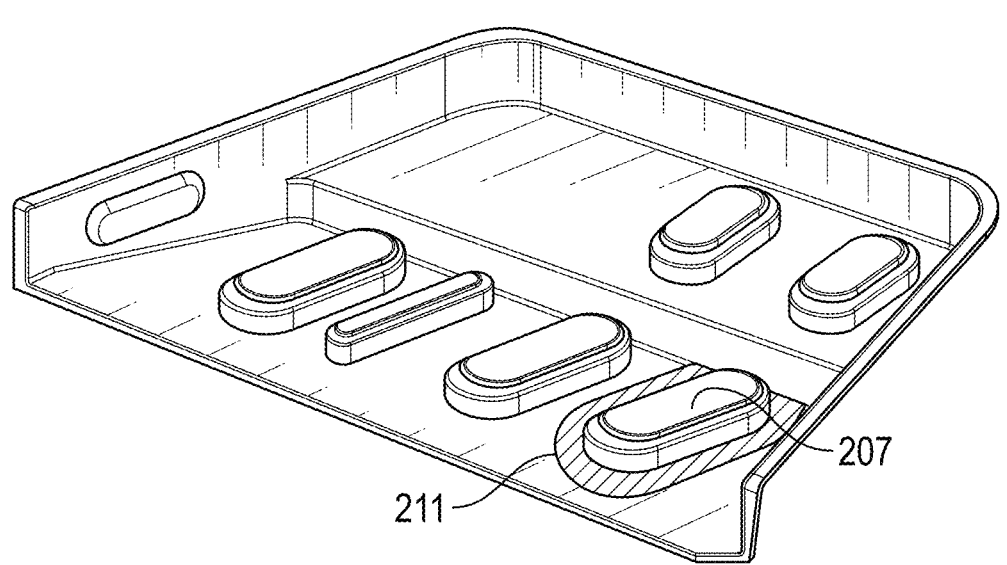
FIGS. 25A, 25B, and 25C illustrate examples of an embodiment of a pedal assembly including dynamic visual indicators configured to provide a contextually-aware indication.
Figure 25B:
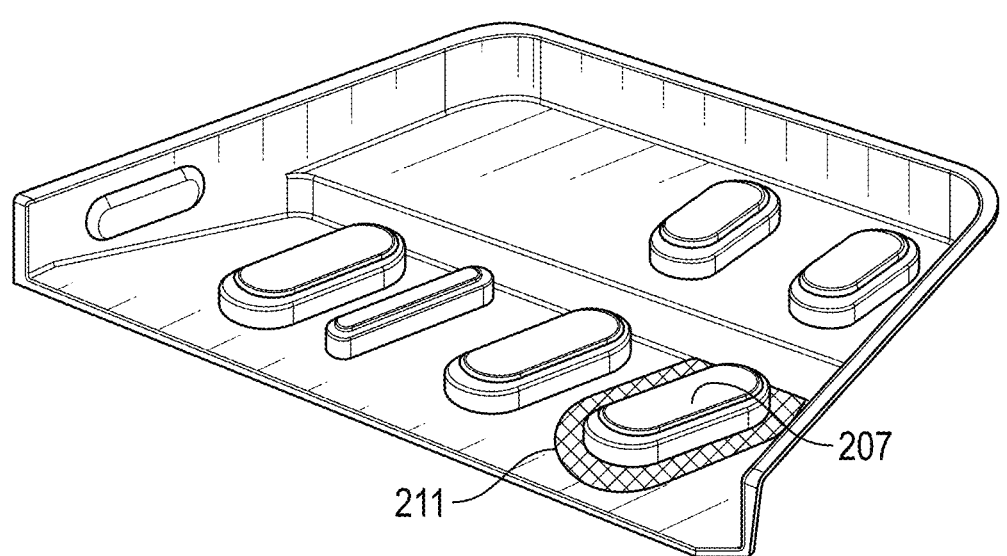
Figure 25C:
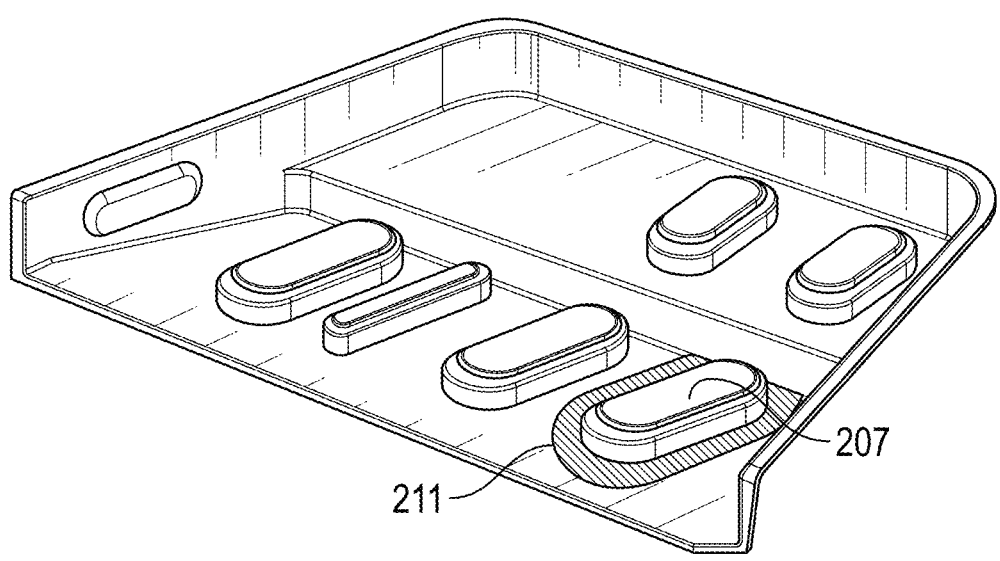

FIGS. 25A-25C provide examples in which an indicator 211 associated with a pedal 207 of a pedal assembly 205 can be considered "contextually-aware." As used in these examples, one or more indicators 211 can be contextually-aware and change or modify the indication that is provided based on the desired function associated with the corresponding pedal 207 at any time. In the examples illustrated in FIGS. 25A-25C, the lower right pedal can be backlit differently with the associated indicator 211 for different functions, as illustrated by the different cross-hatching used in the figures. For example, in FIG. 25A, the lower right pedal 207 is backlit with the indicator 211 in a first color (e.g., the color yellow) when a first instrument (e.g., a monopolar instrument) is ready for activation with the pedal 207. In FIG. 25B, the lower right pedal can be backlit with the indicator 211 in a second color (e.g., a white color) when the instrument is removed. And, as illustrated in FIG. 25C, the indicator 211 can back light the associated pedal 207 with a third color (e.g., an orange color) when a different instrument (e.g., a stapling instrument) is installed and ready for activation by the pedal 207 (e.g., the system is indicating that the stapler is ready for clamping and stapling).

Thus, in these examples, the indicator 211 can be referred to as a "contextually-aware" indicator because the indicator 211 provides different indications for a variety of functions that can be provided by the pedal 207 depending on the context of the system. For example, in FIG. 25A, the context of the system can be that a monopolar instrument of the system is in a ready state for activation. Based on this context, the indicator 211 associated with the lower right pedal 207 can be lit with the first color. In the example of FIG. 25B, the context of the system can be that the instrument has been unloaded. Based on this context, the indicator 211 can be lit with the second color. And, in the example of FIG. 25C, the context of the system can be that a stapler instrument of the system is in a ready state for activation. Based on this context, the indicator 211 can be lit with the third color.

Providing a contextually-aware indication with the indicator 211 can beneficially help a user of the system easily identify a particular function that will be provided when a pedal 207 of the pedal assembly 205 is activated. For example, when the indicator 211 is a contextually-aware indicator, indications provided in different colors can each be associated with corresponding functions. This may help the user to ensure that the he or she understands the function that will be performed when the pedal 207 is actuated. For example, when the user views that that the indicator 211 is providing an indication of the first color (e.g., FIG. 25A), the user will understand that a monopolar instrument is in a ready state for activation and that pressing the pedal 207 will activate the monopolar instrument. Similarly, when the user views that the indicator 211 is providing an indication in the second color (e.g., FIG. 25B), the user will understand that no instrument is currently loaded. And, when the user views that the indicator 211 is providing an indication in the third color (e.g., FIG. 25C), the user may understand that actuating the pedal 207 will activate a stapler instrument.

In the examples described above, the indicators 211 have been described as associated with a user console 200, for example, as shown in FIG. 21. When associated with the user console 200, dynamic indicators 211 associated with foot pedals 207 can provide indications related to user console 200 functions such as, but not limited to, activation of instrument energy, activation of camera control, activation of instrument special functions (e.g. stapling, suture-cutting, etc.), clutching of hand controls, synchronous control of instruments and camera, activation of alternative imaging modes (e.g. fluorescence imaging), adjustment of instrument grip force, switching between control paradigms, switching between actively controlled instruments, and initiation of instrument exchange.

Dynamic indicators 211 as described throughout this section can advantageously be configured for use with foot pedals positioned on other components of a robotic system. For example, in some embodiments, foot pedals with dynamic indicators can also be used on a patient-side component of a robotic system, such as a bed side. As shown in FIGS. 1-15, robotic medical systems can include a patient platform, table, or bed configured to support a patient during a robotic medical system. In some embodiments, aspects of the bed can be robotically controlled. For example, tilt of the patient platform can be robotically controlled. As another example, robotic arms of the system can be configured to be stored below the bed. Moving the robotic arms from a stored position to a deployed position (and vice versa) can be robotically controlled.

Figure 26:
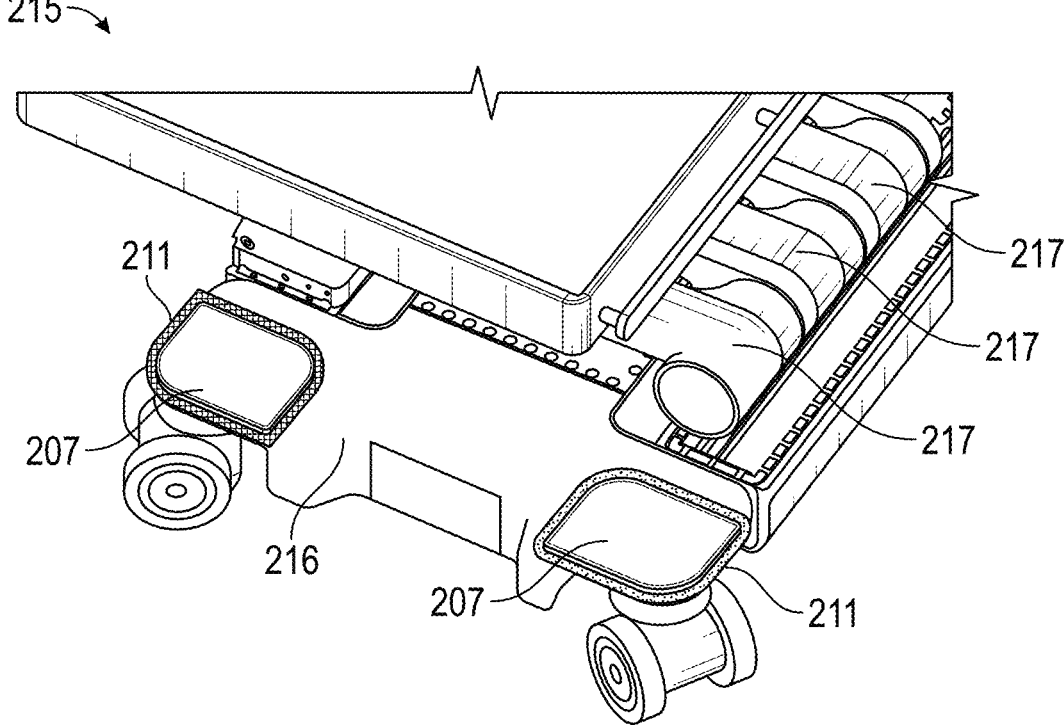
FIG. 26 illustrates a perspective view of a portion of an embodiment of a bed of a robotic medical system including dynamic indicators associated with pedals positioned on a base of the bed.

FIG. 26 illustrates that a bed 215 of a robotic medical system can include dynamic indicators 211. In the illustrated embodiment, dynamic indicators 211 are positioned on pedals 207 on a base 216 of the bed 215. As illustrated, a first dynamic indicator 211 can be configured to provide an indication that actuating the first pedal 207 will deploy the robotic arms 217, and a second dynamic indicator 211 can be configured to provide an indication that actuating the second pedal 207 will stow the robotic arms 217. In the illustrated example, the indicators 211 are configured as perimeter or ring lights surrounding the pedals 207, although other types or placements of indicators 211, such as those described above can be used in other embodiments. In the embodiment of FIG. 26, the dynamic indicator 211 associated with deploying the robotic arms 217 provides an indication in a first color (e.g., yellow), the dynamic indicator 211 associated with stowing the robotic arms 217 provides an indication in a second color (e.g., blue). In this example, the indicators 211 can be constant indicators because particular indications (e.g., the first and second color) can be constantly associated with the corresponding pedals.

In other embodiments, the indicators 211 on the bed 215 can be contextually-aware. For example, in an embodiment, a single pedal on the bed 215 can be associated with both the deploy and stow functions. The indicator 211 associated with the pedal 207 can provide a first indication when actuating the pedal 207 will provide the deploy function, and the indicator 211 associated with the pedal 207 can provide a second indication when actuating the pedal 207 will provide the stow function.

When associated with the patient-side components of a robotic system, such as the bed 215, the dynamic indicators 211 associated with foot pedals 207 can provide indications related to patient-side component functions such as, but not limited to, adjustment of table top or patient position and adjustment of position and orientation of robotic manipulators, such as robotic arms 217.

Figure 27A:
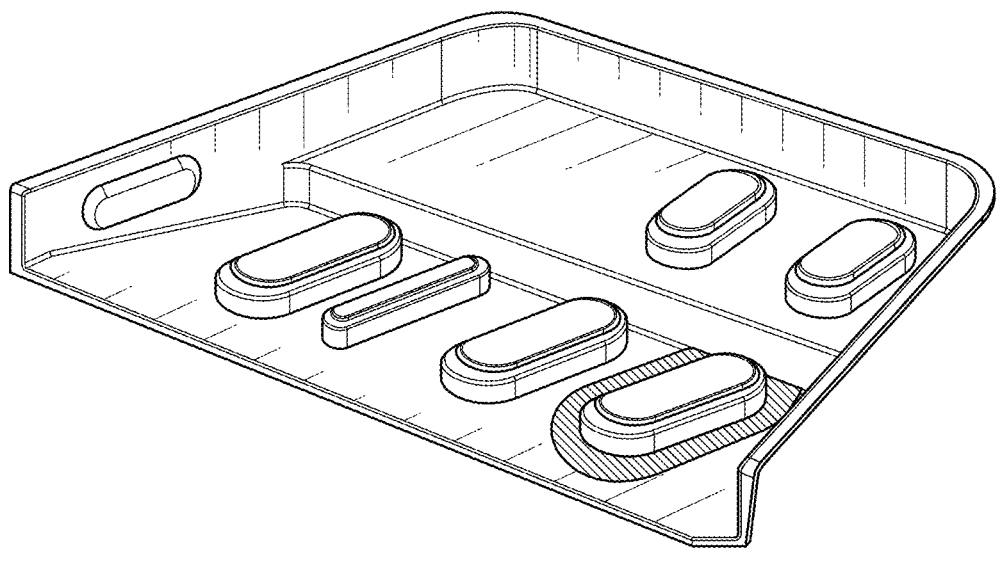
FIGS. 27A and 27B illustrate an embodiment of a pedal assembly and a view in a viewer of a user console and show corresponding dynamic visual indicators in each.
Figure 27B:
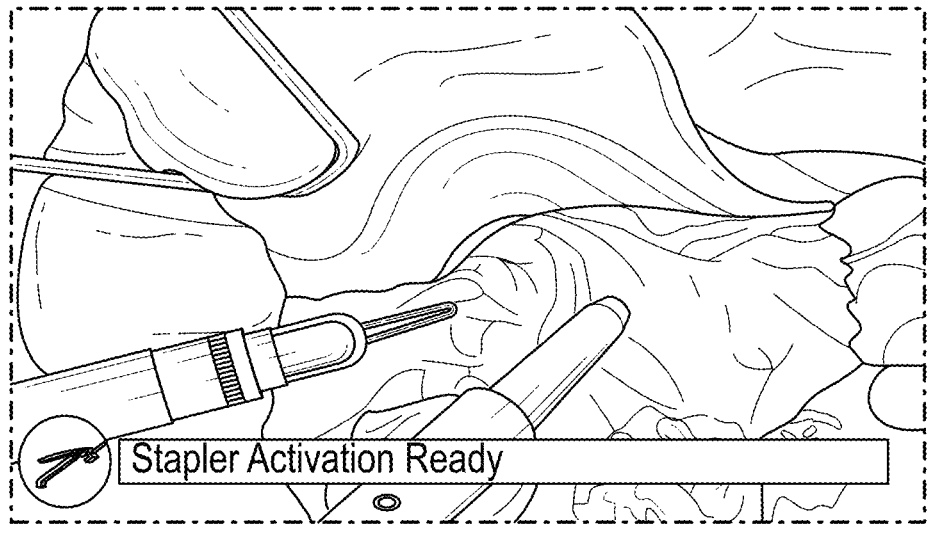
Figure 28:
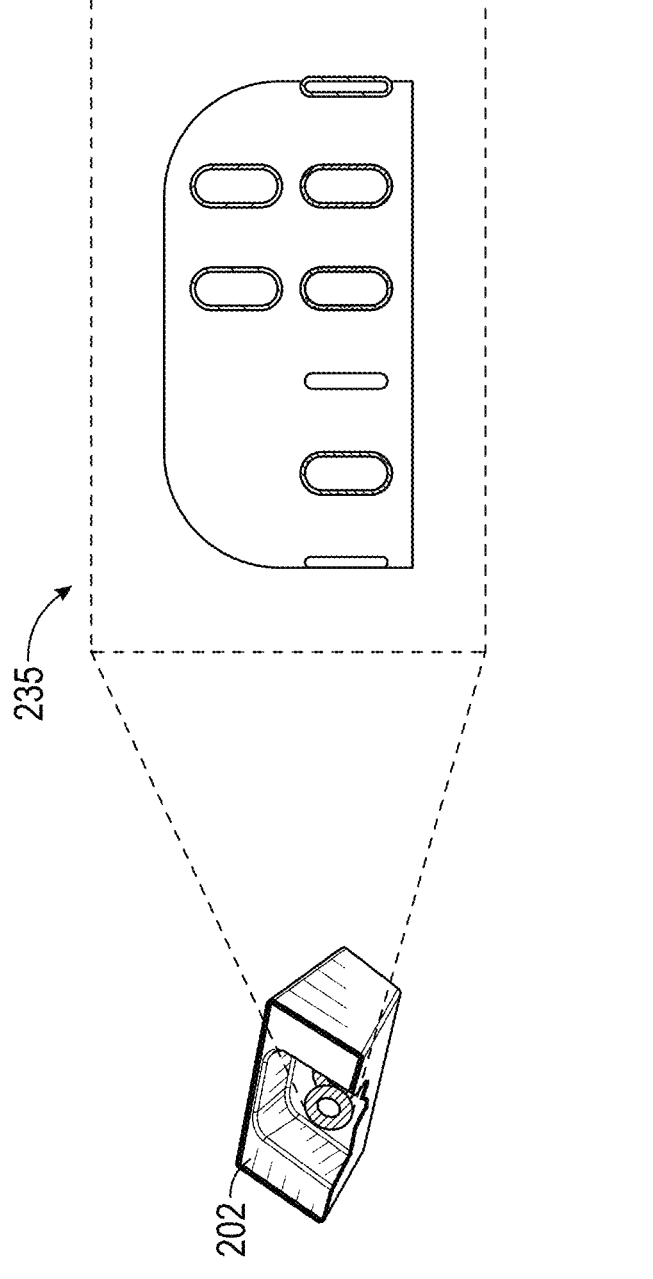
FIG. 28 illustrates that a representation of a pedal assembly including dynamic visual indicators can be displayed in a viewer of a user console.

FIGS. 27A and 27B illustrate that, in some embodiments, visual indicators 211 displayed on the pedals 207 may also be reflected in viewers or monitors viewable by a user (e.g., within the viewer 202). In the example of FIGS. 27A and 27B, an indicator 211 associated with the lower right pedal 207 of a pedal assembly 205 can provide a first indication (e.g., can be lit with a first color as shown in FIG. 27 A) to provide an indication that a stapler of the robotic system is in a ready state for activation. FIG. 27B illustrates a corresponding view within a viewer (such as the viewer 202 of the user console of FIG. 21). As shown in FIG. 27B, a corresponding indicator 225 can be provided within the viewer (e.g., as an overlay on top of a camera view or video feed from a camera). As shown in FIG. 27B, the indicator 225 is shown with an indication that corresponds to the indication provided by the indicator 211 on the pedal assembly. For example, both the indicator 211 (FIG. 27 A) and the indicator 225 (FIG. 27B) can lit or shown with the same color. This can, for example, enhance clarity and communication about which foot pedal 207 is being used and which function will be provided when the foot pedal is actuated. For example, a user may depress a foot pedal with red lighting, and synchronously a red visual indicator may appear on a monitor for the user. Notably, different colors and hues associated with a single foot pedal can be visible on the viewer and pedal assembly. Alternatively, a user may be able to call up a view 235 of the foot pedals within the viewer 202 as a reminder about which pedals 207 perform which functions, as shown in FIG. 28. Within the view 235 of the foot pedals, indications corresponding to the indicators 211 provided on the pedal assembly can be displayed, e.g., as a graphical depiction of the pedal assembly and/or as an overlay on top of another image.

Although the examples of FIGS. 27A-28 have been described with reference to the viewer 202 of the user console 200, these features can also be displayed on other monitors of the robotic system. For example, these features can be displayed on head-in viewers (2D or 3D), operating room monitors, console monitors, or touchscreens, among others.

FIG. 29 illustrates an example method 300 for implementing dynamic indicators on a robotic medical system as described herein. The method 300 begins at block 302, which comprises receiving a first input from an operator to change a state of a medical instrument from a non-active to an active state. For example, when an operator is controlling an energy delivery instrument, the operator can press then pedal to change the state of the instrument from a non-active state to a ready state for energy delivery (e.g., an active state in which, upon pressing the pedal again, the energy delivery instrument will deliver energy to the patient). In some embodiments, the first input can comprise receiving the user input at a user console (e.g., as shown in FIG. 21). For example, the user input can be provided via the controllers 203 and/or the pedal assembly 205. In some embodiments, the user input is provided by the user depressing a pedal 207 of the pedal assembly.

At block 304, the method 300 comprises activating a dynamic indicator 211 associated with a foot pedal 207 of the robotic medical system to indicate that the medical instrument is in the active state. In some embodiments, the dynamic indicator 211 comprises a visual indicator, such as a light. Activating the dynamic indicator 211 can comprise illuminating the food pedal with the light. In some embodiments, the dynamic indicator 211 comprises a haptic indicator, and activating the dynamic indicator 211 comprises providing a haptic indication.

At block 306, the method 300 comprises receiving a second input from the operator, via the foot pedal, to deliver energy to a surgical site with the medical instrument. In some embodiments, the second input can comprise receiving the user input at a user console (e.g., as shown in FIG. 21). For example, the second user input can be provided via the controllers 203 and/or the pedal assembly 205. In some embodiments, the second user input is provided by the user depressing a pedal 207 of the pedal assembly. The pedal 207 can be the same or a different pedal 207 as the pedal 207 described in block 302.

Finally, at block 308, the method 300 comprises delivering energy to the surgical site with the medical instrument. In some embodiments, the dynamic indicator 211 continues to be active while delivering energy from the instrument to the surgical site.

Figure 30:
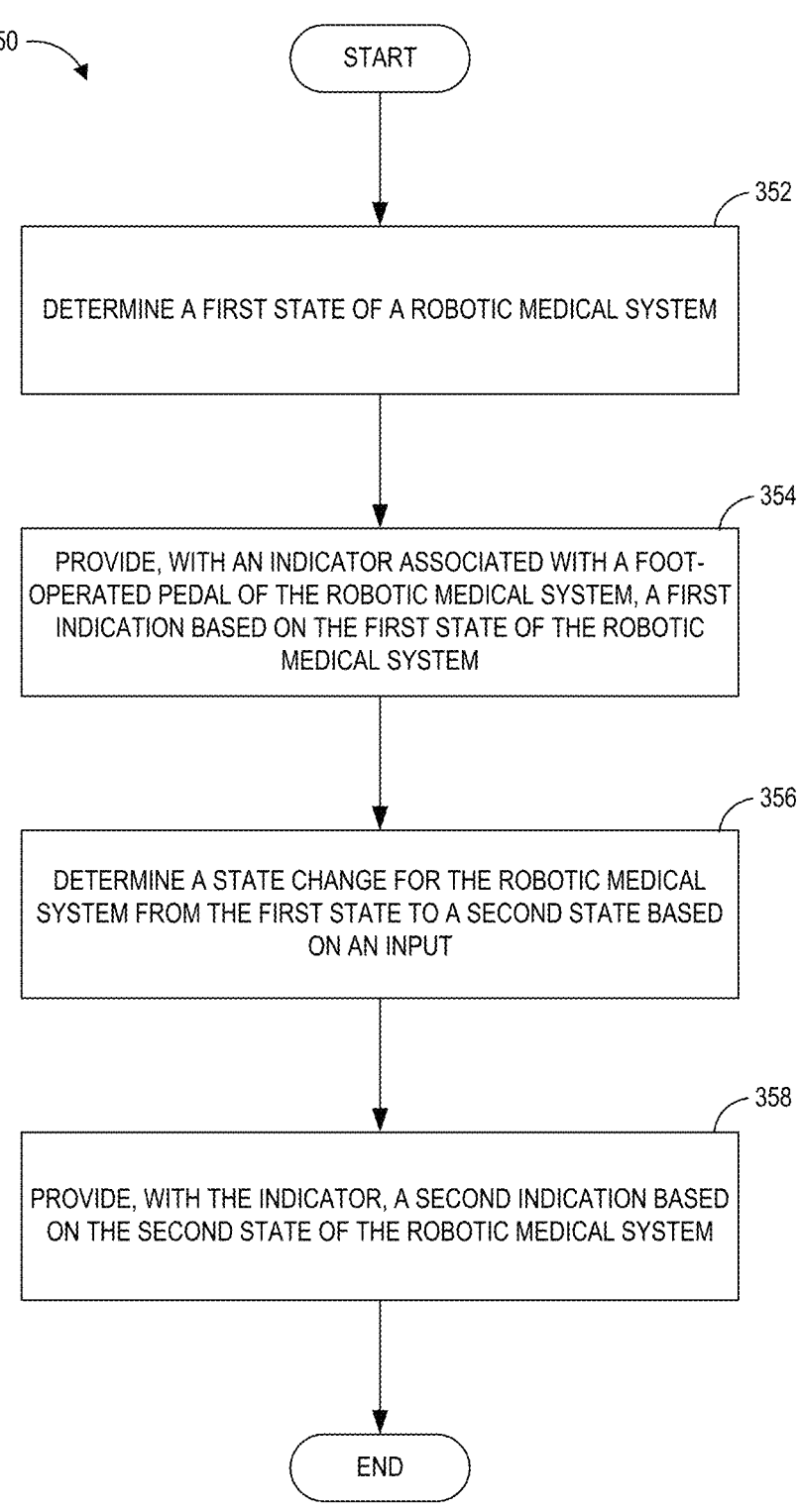
FIG. 30 is a flow chart depicting a second example method for implementing dynamic indicators for a robotic medical system.

FIG. 30 illustrates another example method 350 for implementing dynamic indicators on a robotic medical system as described herein. The method 350 begins at block 352, which comprises determining a first state of a robotic medical system. The first state can be determined based on a variety of factors, such as those described above and/or as well as one or more of the following:

A medical instrument of coupled to the robotic system. For example, an instrument attached to a robotic arm can communicate information about the instrument to the system through the robotic arm. The state of the robotic system can be determined based on the type of medical instrument or a state of the medical instrument (e.g., whether delivering energy to the patient or not).

A robotic arm of the robotic medical system. In some embodiments, the robotic arm itself can have information to convey state. For example, the robotic arm can communicate information related to its position and/or potential faults (e.g., collisions with other arms).

The robotic system itself. For example, the robotic system can determine if a currently selected medical instrument is located outside of current field of view.

Surgeon input information from the surgeon's hands at the master controller of the console.

The console itself can convey from which state information can be determined.

Pedals of the robotic system. For example, state can be determined based on whether one or more of the pedals have been pressed. Once a pedal is pressed, the state of the system can change.

At block 354, the method 350 comprises providing, with an indicator 211 associated with a foot-operated pedal 207 of the robotic medical system, a first indication based on the first state of the robotic medical system. In some embodiments, the dynamic indicator 211 comprises a visual indicator, such as a light. Providing the indication with the dynamic indicator 211 can comprise illuminating the food pedal with the light. In some embodiments, the dynamic indicator 211 comprises a haptic indicator, and providing the indication with the indicator 211 comprises providing a haptic indication.

At block 356, the method 350 comprises determining a state change for the robotic medical system from the first state to a second state based on an input. In some embodiments, the user input can be provided via the user console 200 (e.g., as shown in FIG. 21). For example, the user input can be provided via the controllers 203 and/or the pedal assembly 205. In some embodiments, the user input is provided by the user depressing a pedal 207 of the pedal assembly 205. In addition to the user input, the second state can be determined based on a variety of factors, such as those described.

Finally, at block 358, the method 350 can comprise providing, with the indicator 211, a second indication based on the second state of the robotic medical system. In some embodiments, the second indication is different than the first indication. For example, in the case of a visual indicator, the first indication can be a light of the first color, and the second indication can be a light of a second color.

3. Implementing Systems and Terminology.

Implementations disclosed herein provide systems, methods and apparatus associated with foot pedal assemblies with dynamic visual indicators configured for use with robotic medical systems.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

Any phrases referencing specific computer-implemented processes/functions described herein may be stored as one or more instructions on a processor-readable or computer-readable medium. The term "computer-readable medium" refers to any available medium that can be accessed by a computer or processor. By way of example, and not limitation, such a medium may comprise random access memory (RAM), read-only memory (ROM), electrically erasable programmable read-only memory (EEPROM), flash memory, compact disc read-only memory (CD-ROM) or other optical disk storage, magnetic disk storage or other magnetic storage devices, or any other medium that can be used to store desired program code in the form of instructions or data structures and that can be accessed by a computer. It should be noted that a computer-readable medium may be tangible and non-transitory. As used herein, the term "code" may refer to software, instructions, code or data that is/are executable by a computing device or processor.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

The previous description of the disclosed implementations is provided to enable any person skilled in the art to make or use the present invention. Various modifications to these implementations will be readily apparent to those skilled in the art, and the generic principles defined herein may be applied to other implementations without departing from the scope of the invention. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Thus, the present invention is not intended to be limited to the implementations shown herein but is to be accorded the widest scope consistent with the principles and novel features disclosed herein.

What is claimed is:

1. A medical system comprising:
a first robotic medical instrument, the first robotic medical instrument being operable to deliver electrical energy to tissue;
a second robotic medical instrument, the second robotic medical instrument being operable to perform one or more of stapling, suction, irrigation, or suture cutting;
a foot pedal assembly comprising:
one or more pedals configured to be foot operated; and
a dynamic indicator associated with a first pedal of the one or more pedals, the dynamic indicator positioned on the foot pedal assembly and configured to:
provide a first indication when the first pedal is associated with the first robotic medical instrument, and
provide a second indication when the first pedal is associated with the second robotic medical instrument; and
a processor in communication with memory stored instructions that, when executed, cause the processor to:
determine whether the first pedal is associated with the first robotic medical instrument or the second robotic medical instrument;
cause the dynamic indicator to provide the first indication in response to a determination that the first pedal is associated with the first robotic medical instrument; and
cause the dynamic indicator to provide the second indication in response to a determination that the first pedal is associated with the second robotic medical instrument.

2. The medical system of claim 1, further comprising:
at least one robotic arm configured to perform a surgical procedure, either the first robotic medical instrument or the second robotic medical instrument being coupled to the at least one robotic arm.

3. The medical system of claim 2, wherein:
the processor is further configured to:
determine an instrument status indicative of the first robotic medical instrument being in a ready state for energy delivery, and

provide a third indication that the first robotic medical instrument is in the first state based on the determined instrument status being in the ready state for energy delivery.

4. The medical system of claim 3, wherein the dynamic indicator comprises a dynamic visual indicator having a light and the first indication comprises a lit state of the dynamic visual indicator.

5. The medical system of claim 4, wherein the light is configured such that the first indication comprises a first color and the second indication comprises a second color.

6. The medical system of claim 1, wherein:
the dynamic indicator is a haptic indicator; or
the dynamic indicator is a sound-based indicator.

7. The medical system of claim 1, wherein the processor is further configured to cause the dynamic indicator to provide a third indication, the third indication being provided in response to the first robotic medical instrument or the second robotic medical instrument being activated.

8. A console for a medical system, the console comprising:
a base;
one or more hand-operated controllers, a first hand-operated controller of the one or more hand-operated controllers being operable to control a robotic medical instrument;
a viewer configured to display images; and
a foot-operated pedal assembly positioned at the base, the foot-operated pedal assembly comprising:
a plurality of pedals configured to be foot operated, the plurality of pedals including a first pedal associated with the robotic medical instrument; and
a plurality of dynamic indicators, each dynamic indicator of the plurality of dynamic indicators associated with one pedal of the plurality of pedals, a first dynamic indicator of the plurality of dynamic indicators being configured to:
provide a first indication when the robotic medical instrument is in a first state, the first pedal being actuable when the robotic medical instrument is in the first state, the first hand-operated controller of the one or more hand-operated controllers being operable to control the robotic medical instrument when the robotic medical instrument is in the first state, and
provide a second indication when the robotic medical instrument is in a second state, the first pedal being actuable when the robotic medical instrument is in the second state, the first hand-operated controller of the one or more hand-operated controllers being operable to control the robotic medical instrument when the robotic medical instrument is in the second state.

9. The console of claim 8, wherein:
each dynamic indicator of the plurality of dynamic indicators comprises a light;
the first indication comprises an unlit state of the light; and
the second indication comprises a lit state of the light.

10. The console of claim 8, wherein:
each dynamic indicator of the plurality of dynamic indicators comprises a light;
the first indication comprises a first lit state of the light, wherein the first lit state comprises a first color; and
the second indication comprises a second lit state of the light, wherein the second lit state comprises a second color.

11. The console of claim 8, wherein each dynamic indicator of the plurality of dynamic indicators comprises a light and at least one of the first indication and the second indication comprises:
a first pattern of activating and deactivating the light; or
a first brightness of the light; and
the other of the first indication and the second indication comprises:
a second pattern of activating and deactivating the light; or
a second brightness of the light.

12. The console of claim 8, wherein:
the first pedal of the plurality of pedals is selectively actuable between a deactivated state and an activated state; and
each dynamic indicator of the plurality of dynamic indicators is configured to provide the first indication, the second indication, and a third indication.

13. The console of claim 12, wherein:
the deactivated state comprises an unpressed state of the first pedal; and
the activated state comprises a pressed state of the first pedal.

14. The medical system of claim 1, wherein:
the foot pedal assembly further comprises a pedal board;
the one or more pedals comprise a plurality of pedals positioned on the pedal board; and
the dynamic indicator includes a plurality of dynamic visual indicators positioned on surfaces of the pedal board at locations associated with the pedals to which the dynamic visual indicators correspond.

15. The medical system of claim 1, wherein:
the foot pedal assembly further comprises a pedal board;
the one or more pedals comprise a plurality of pedals positioned on the pedal board; and
the dynamic indicator includes a plurality of dynamic visual indicators positioned on surfaces of the pedals to which the dynamic visual indicators correspond.

16. The medical system of claim 1, further comprising:
a surgeon console, the surgeon console comprising a viewer and the foot pedal assembly, wherein the memory stored instructions, when executed, further cause the processor to:
display an additional indicator in the viewer as an overlay on a video feed, wherein the additional indicator reflects the dynamic indicator positioned on the foot pedal assembly.

17. A medical system comprising:
a robotic medical instrument;
a robotic arm assembly;
a foot pedal assembly comprising:
one or more pedals configured to be foot operated; and
a dynamic indicator associated with a first pedal of the one or more pedals, the dynamic indicator positioned on the foot pedal assembly and configured to:
provide a first indication when the robotic medical instrument is in a first state, the robotic medical instrument being coupled with the robotic arm assembly when the robotic medical instrument is in the first state, and
provide a second indication when the robotic medical instrument is in a second state, the robotic medical instrument being decoupled from the robotic arm assembly when the robotic medical instrument is in the second state; and a processor in communication with memory stored instructions that, when executed, cause the processor to:

determine a state of the robotic medical instrument;

cause the dynamic indicator to provide the first indication in response to the determined state comprising the first state; and cause the dynamic indicator to provide the second indication in response to the determined state comprising the second state.

* * * * *